United States Patent
Okamoto et al.

(10) Patent No.: US 11,667,594 B2
(45) Date of Patent: Jun. 6, 2023

(54) METHOD FOR PRODUCING 1,2-DICHLORO-3,3-DIFLUORO-1-PROPENE AND SOLVENT COMPOSITION

(71) Applicant: CENTRAL GLASS COMPANY, LIMITED, Yamaguchi (JP)

(72) Inventors: Masamune Okamoto, Saitama (JP); Kei Matsunaga, Saitama (JP); Hideaki Imura, Saitama (JP); Shota Kawano, Saitama (JP)

(73) Assignee: CENTRAL GLASS COMPANY, LIMITED, Yamaguchi (JP)

( * ) Notice: Subject to any disclaimer, the term of this patent is extended or adjusted under 35 U.S.C. 154(b) by 0 days.

(21) Appl. No.: 17/725,810

(22) Filed: Apr. 21, 2022

(65) Prior Publication Data

US 2022/0251008 A1 Aug. 11, 2022

Related U.S. Application Data

(60) Division of application No. 16/984,848, filed on Aug. 4, 2020, now Pat. No. 11,339,106, which is a continuation of application No. PCT/JP2019/004119, filed on Feb. 5, 2019.

(30) Foreign Application Priority Data

Feb. 16, 2018 (JP) .............................. JP2018-026033

(51) Int. Cl.
| | | |
|---|---|---|
| C07C 21/18 | (2006.01) | |
| C07C 17/20 | (2006.01) | |
| C09K 3/30 | (2006.01) | |
| C09K 5/04 | (2006.01) | |
| C10M 131/04 | (2006.01) | |
| C11D 7/50 | (2006.01) | |

(52) U.S. Cl.
CPC ............ *C07C 17/206* (2013.01); *C07C 21/18* (2013.01); *C09K 3/30* (2013.01); *C09K 5/044* (2013.01); *C09K 2205/126* (2013.01); *C10M 131/04* (2013.01); *C11D 7/5018* (2013.01)

(58) Field of Classification Search
None
See application file for complete search history.

(56) References Cited

U.S. PATENT DOCUMENTS

| 2011/0031436 A1 | 2/2011 | Mahler et al. |
| 2015/0105596 A1 | 4/2015 | Wang et al. |
| 2017/0297982 A1 | 10/2017 | Deur-Bert et al. |

FOREIGN PATENT DOCUMENTS

| CN | 102015957 | 4/2011 |
| CN | 105829270 | 8/2016 |
| CN | 105849072 | 8/2016 |
| JP | 2011-520017 | 7/2011 |
| JP | 2016-537319 | 12/2016 |
| WO | 2009/137658 | 11/2009 |
| WO | 2018/193884 | 10/2018 |
| WO | 2019/189024 | 10/2019 |

OTHER PUBLICATIONS

Office Action dated Sep. 21, 2022, in corresponding Chinese Patent Application No. 201980011905.X, with English translation.
Whaley et al., "Isomerization During Allylic Fluorination", J. Am. Chem. Soc., 1948, vol. 70, pp. 1026-1027.
Belter et al., "1-Chloro3, 3-difluoropropadiene", Journal of Fluorine Chemistry, 1999, vol. 94, No. 1, pp. 61-63.
International Search Report dated May 7, 2019 in International (PCT) Application No. PCT/JP2019/004119.
Written Opinion of the International Searching Authority dated May 7, 2019 in International (PCT) Application No. PCT/JP2019/004119.
Partial Supplementary European Search Report dated Oct. 29, 2021, in corresponding Emopean Patent Application No. 19754754.0.
Extended European Search Report dated Jan. 31, 2022 in corresponding European Patent Application No. 19754754.0.
Bondi, Anthony et al., "Re-identification of $C_3HClF_2$ by analysis of its Diels-Alder products", Journal of Fluorine Chemistry, 2005, vol. 126, pp. 1549-1552.
Hauptschein, Murray et al., "The Directing Influence of Substituents on the Chlorination of Halogenated Ethanes and Propanes", Journal of the American Chemical Society, 1951, pp. 5591-5593.
Office Action dated Nov. 22, 2022 in Japanese Patent Application No. 2020-500421, with English-language translation.
Prins, H. J. et al., "Syntheses of Polychloro-Compounds. II.: The catalytic action of aluminium chloride in the reaction between chloroform and dichloroethylene", Recueil des Travaux Chimiques des Pays-Bas, 1935, vol. 54, Issue 4, pp. 307-312.
Heilbron, I. M. et al., "The Direct Synthesis of 2'-Halogenomesobenzanthrones", Journal of the Chemical Society, 1936, pp. 781-785.
Office Action dated Apr. 8, 2023, in corresponding Chinese Patent Applicant No. 201980011905.X, with English translation.

*Primary Examiner* — Medhanit W Bahta
(74) *Attorney, Agent, or Firm* — Wenderoth, Lind & Ponack, L.L.P.

(57) ABSTRACT

By fluorinating 1,2,3,3-tetrachloro-1-propene (1230xd) using hydrogen fluoride as a fluorinating agent, an efficient method for producing 1,2-dichloro-3,3-difluoro-1-propene (1232xd) is provided. Through this composition including 1232xd, there are also provided an environmentally friendly composition having excellent ability to dissolve various organic matters, a method for cleaning an article using the composition, a method for producing a lubricant solution using the composition, and a method for producing a component provided with a lubricant coating film.

20 Claims, No Drawings

METHOD FOR PRODUCING 1,2-DICHLORO-3,3-DIFLUORO-1-PROPENE AND SOLVENT COMPOSITION

CROSS REFERENCE TO RELATED APPLICATION

This application is based upon and claims the benefit of priority from the prior Japanese Patent Application No. 2018-026033, filed on Feb. 16, 2018. Further, this application is the National Phase Application of International Application No. PCT/JP2019/004119, filed on Feb. 5, 2019. Both of the priority documents are hereby incorporated by reference in their entireties.

FIELD

The present invention relates to a method of the production of 1,2-dichloro-3,3-difluoro-1-propene (hereinafter also referred to as 1232xd) and a process of the co-production of 1232xd and 1,2,3-trichloro-3-fluoro-1-propene (hereinafter also referred to as 1231xd). The present invention also relates to a solvent composition comprising 1232xd, and a cleaning method of articles, a method for producing a lubricant solution and an article with a lubricant coating film, which use the solvent composition.

BACKGROUND

Hydrofluoroolefins (hereinafter also referred to as HFO) have a lower global warming potential (GWP) than hydrochlorofluorocarbons (HCFC compound) such as 1,3-dichloro-1,1,2,2,2-pentafluoropropane (225 ca), and are more Earth-environmentally friendly compounds, and so they are being replaced for various applications. 1232xd and 1231xd are also types of HFO compounds.

Few methods for producing 1232xd and 1231xd are known, and it is disclosed in "A. M. WHLEY and H. W. DAVIS J. Am. Chem. Soc., 1948, p. 1026-1027" that 1232xd is obtained by reacting 1,2,3,3-tetrachloro-1-propene (hereinafter also referred to as 1230xd) and 1 equivalent of antimony trifluoride at 100° C.

Since the reaction described in "A. M. WHLEY and H. W. DAVIS J. Am. Chem. Soc., 1948, p. 1026-1027" requires the same amount of antimony fluoride, the environmental load is large, and there is room for improvement in mass production.

Thus, it cannot be said that a method for producing 1232xd has been developed sufficiently, and a more efficient method for producing 1232xd is required.

SUMMARY

The present invention has been made in view of the above. It is an object of the present invention to provide an efficient method for producing 1,2-dichloro-3,3-difluoro-1-propene (1232xd). It is an object of the present invention to provide a solvent composition containing 1232xd which is excellent in solubility of various organic substances and is Earth-environmentally friendly, a method of cleaning articles using the solvent composition, a method of producing a lubricant solution using the solvent composition, and a method of producing an article with a lubricant coating film.

As a result of intensive studies to solve the above-mentioned problems, the present inventors have found that the above-mentioned problems can be solved and have completed the present invention. That is, the present invention includes the following inventions.

[Invention 1]
A method of producing 1,2-dichloro-3,3-difluoro-1-propene comprises a step of fluorinating 1,2,3,3-tetrachloro-1-propene with hydrogen fluoride.

[Invention 2]
The method according to the invention 1, wherein hydrogen fluoride is used at 2 mol or more and 40 mol or less for 1 mol of 1,2,3,3-tetrachloro-1-propene.

[Invention 3]
The method according to the invention 1, wherein the fluorinating is performed in a liquid phase.

[Invention 4]
The method according to the invention 3, wherein the fluorinating is performed at a temperature of 100° C. or more and 200° C. or less.

[Invention 5]
The method according to the invention 1, wherein the fluorinating is performed in a vapor phase.

[Invention 6]
The method according to the invention 5, wherein the fluorinating is performed at a temperature of 100° C. or more and 500° C. or less.

[Invention 7]
The method according to any one of the inventions 1 to 6, wherein 1,2,3-trichloro-3-fluoro-1-propene is produced together with 1,2-dichloro-3,3-difluoro-1-propene by the fluorinating.

[Invention 8]
The method according to the invention 7, wherein the produced 1,2,3-trichloro-3-fluoro-1-propene is provided for the fluorinating.

[Invention 9]
A method of producing 1,2-dichloro-3,3-difluoro-1-propene by fluorinating a composition includes 1,2,3,3-tetrachloro-1-propene and 1,2,3-trichloro-3-fluoro-1-propene with hydrogen fluoride.

[Invention 10]
A method of producing both 1,2-dichloro-3,3-difluoro-1-propene and 1,2,3-trichloro-3-fluoro-1-propene comprises a step of fluorinating 1,2,3,3-tetrachloro-1-propene with hydrogen fluoride.

[Invention 11]
The method according to the invention 10, wherein the hydrogen fluoride is used at 2 mol or more and 40 mol or less for 1 mol of 1,2,3,3-tetrachloro-1-propene.

[Invention 12]
The method according to the invention 10, wherein the fluorinating is performed in a liquid phase.

[Invention 13]
The method according to the invention 12, wherein the fluorinating is performed at a temperature of 100° C. or more and 200° C. or less.

[Invention 14]
The method according to the invention 10, wherein the fluorinating is performed in a vapor phase.

[Invention 15]
The method according to the invention 14, wherein the fluorinating is performed at a temperature of 100° C. or more and 500° C. or less.

[Invention 16]
A method according to any one of the inventions 1 to 15 comprises a step of obtaining 1,2,3,3-tetrachloro-1-propene by contacting 1,1,2,3,3-pentachloropropane with an aqueous solution of an inorganic base in a liquid phase.

[Invention 17]

The method according to the invention 16 comprises a step of obtaining 1,1,2,3,3-pentachloropropane by reacting 1,2-dichlroroethylene and chloroform under a presence of a Lewis acid catalyst.

[Invention 18]

The method according to the invention 17, wherein chloroform is used in an amount of more than 1 mol for 1 mol of 1,2-dichloroethylene.

[Invention 19]

A solvent composition comprises cis-1,2-dichloro-3,3-difluoro-1-propene.

[Invention 20]

A solvent composition comprises cis-1,2-dichloro-3,3-difluoro-1-propene and trans-1,2-dichloro-3,3-difluoro-1-propene.

[Invention 21]

A solvent composition comprises trans-1,2-dichloro-3,3-difluoro-1-propene.

[Invention 22]

The solvent composition according to any one of the inventions 19 to 21, further comprises 1,2,3-trichloro-3-fluoro-1-propene.

[Invention 23]

The solvent composition according to the inventions 19 to 22, further comprises at least one organic compound selected from a group consisting of hydrocarbons, alcohols, ketones, ethers, esters, chlorocarbons, HFCs and HFEs.

[Invention 24]

The solvent composition according to any one of the inventions 19 to 23, further comprises at least one additive agent selected from a group consisting of a stabilizer, a surfactant, a flame retardant, a metal passivator, and a corrosion inhibitor.

[Invention 25]

An aerosol composition comprises the solvent composition according to any one of the inventions 19 to 24, and injection gas.

[Invention 26]

A cleaning method of an article comprises a step of contacting the article with the solvent composition or the aerosol composition according to any one of the inventions 19 to 25.

[Invention 27]

A method for producing a lubricant solution comprises obtaining the lubricant solution by diluting a lubricant agent with the solvent composition or the aerosol composition according to any one of the inventions 19 to 25.

[Invention 28]

A method for producing an article with a lubricant, comprises coating a lubricant solution including a lubricant agent and the solvent composition or the aerosol composition according to any one of the inventions 19 to 25, and vaporizing the solvent composition or the aerosol composition from the article to form a coating film including the lubricant agent on a surface of the article.

[Invention 29]

A cleaning agent comprises the solvent composition or the aerosol composition according to any one of the inventions 19 to 25.

[Invention 30]

A draining agent comprises the solvent composition or the aerosol composition according to any one of the inventions 19 to 25.

[Invention 31]

A foaming agent comprises the solvent composition or the aerosol composition according to any one of the inventions 19 to 25.

[Invention 32]

A heat transfer medium comprises the solvent composition according to any one of the inventions 19 to 24.

[Invention 33]

An organic Rankine cycle system uses the heat transfer medium according to the invention 32.

[Invention 34]

A high-temperature heat pump cycle system uses the heat transfer medium according to the invention 32.

[Invention 35]

A refrigeration cycle system uses the heat transfer medium according to the invention 32.

[Invention 36]

A fire extinguishing composition comprises 1,2-dichloro-3,3-difluoro-1-propene and at least nonflammable gas except for 1,2-dichloro-3,3-difluoro-1-propene.

According to the present invention, an efficient method for the production of 1,2-dichloro-3,3-difluoro-1-propene (1232xd) can be provided. Furthermore, according to the present invention, it is possible to provide a solvent composition containing 1232xd which is excellent in solubility of various organic substances and is Earth-environmentally friendly, a method of cleaning an article using the solvent composition, a method of producing a lubricant solution using the solvent composition, and a method of producing an article with a lubricant coating film.

DESCRIPTION OF EMBODIMENTS (Description of Terms)

As used herein, unless otherwise specified, 1230xd means cis isomer, trans isomer, or a mixture thereof of 1,2,3,3-tetrachloro-1-propene. Unless otherwise specified, 1231xd means the cis isomer, the trans isomer, or the mixture thereof of 1,2,3-trichloro-3-fluoro-1-propene. Unless otherwise specified, 1232xd means the cis isomer, the trans isomer, or the mixture thereof of 1,2-dichloro-3,3-difluoro-1-propene. Unless otherwise specified, 1,2-dichloroethylene means the cis isomer, the trans isomer, or the mixture thereof.

In the present specification, "co-production of 1232xd and 1231xd" means that 1232xd and 1231xd are produced at least by the reaction according to the present invention, and preferably 1231xd is produced in an amount of 0.0001 mol or more, particularly preferably 0.001 mol or more per 1 mol of 1232xd.

Hereinafter, the present invention will be described. The present invention is not limited to the following embodiments, and the present invention is also treated as encompassed by modifications and improvements appropriately made to the following embodiments based on the ordinary knowledge of a person skilled in the art without departing from the spirit of the present invention.

<Fluorination of 1,2,3,3-tetrachloro-1-propene (1230xd)>

In one embodiment of the present invention, 1230xd is fluorinated with hydrogen fluoride used as a fluorination agent. Thus, it is possible to produce 1232xd.

In one embodiment, 1231xd can be produced by fluorination of 1230xd.

In one embodiment, 1230xd of fluorination can co-produce 1232xd and 1231xd.

(1230xd)

1230xd is a known compound. A suitable example of the producing method thereof will be described later, but this does not preclude adoption of other producing methods.

In one embodiment of the present invention, 1231xd may be provided to fluorination with 1230xd in the fluorination of 1230xd for producing 1232xd.

(Hydrogen Fluoride)

In the fluorination of 1230xd, the amount of hydrogen fluoride used is not particularly limited as long as a target product can be obtained by the fluorination of 1230xd. Normally, hydrogen fluoride is used in more than a stoichiometric for 1 mol of 1230xd. The upper limit is not particularly limited but is preferably 40 mol or less from the viewpoint of economical production. The amount of hydrogen fluoride used is expressed relative to the charge amount of 1230xd when the reaction type is batch or semi-batch, and relative to the steady amount of 1230xd present in a reactor when the reaction type is continuous.

In one embodiment, to produce 1232xd advantageously, 3 mol or more and 40 mol or less, preferably 4 mol or more and 30 mol or less, more preferably 8 mol or more and 20 mol or less of hydrogen fluoride is used per 1 mol of 1230xd.

In one embodiment, to advantageously produce 1231xd, 1 mol or more and 20 mol or less, preferably 2 mol or more and 15 mol or less, more preferably 4 mol or more and 10 mol or less of hydrogen fluoride is used per 1 mol of 1230xd.

In one embodiment, to co-produce 1231xd and 1232xd dominantly, 2 mol or more and 40 mol or less, preferably 3 mol or more and 30 mol or less, more preferably 4 mol or more and 20 mol or less, and still more preferably 8 mol or more and 20 mol or less of hydrogen fluoride is used per 1 mol of 1230xd.

<Fluorination of 1230xd in Liquid Phase>

In one embodiment, the fluorination of 1230xd by hydrogen fluoride can be performed in a liquid phase.

The fluorination of 1230xd in the liquid phase may be performed in any of batch, semi-continuous and continuous flow systems.

(Temperature)

In the fluorination of 1230xd in the liquid phase, the temperatures are not particularly limited as long as the target product can be produced. The fluorination of 1230xd is usually carried out at 0° C. or more and 200° C. or less, preferably 100° C. or more and 200° C. or less.

In one embodiment, since 1232xd can be advantageously produced, the fluorination of 1230xd is performed at 100° C. or more and 200° C. or less, preferably 110° C. or more and 200° C. or less, particularly preferably 130° C. or more and 200° C. or less, more preferably 150° C. or more and 200° C. or less.

In one embodiment, when it is desired to predominantly produce 1231xd, the fluorination of 1230xd is carried out at 0° C. or more and 180° C. or less, preferably 20° C. or more and 150° C. or less, particularly preferably 40° C. or more and 130° C. or less, and more preferably 60° C. or more and 130° C. or less.

In one embodiment, when 1232xd and 1231xd are co-produced, fluorination of 1230xd is carried out at 0° C. or more and 200° C. or less, preferably 40° C. or more and 180° C. or less, particularly preferably 80° C. or more and 180° C. or less, more preferably 100° C. or more and 150° C. or less.

(Pressure)

In the fluorination of 1230xd in the liquid phase, the pressure is not particularly limited as long as the target product can be produced. Generally, the fluorination of 1230xd in the liquid phase is carried out either under normal pressure (under atmospheric pressure) or under pressure, preferably under pressure. In one embodiment of the present invention, the fluorination of 1230xd is carried out at 0.1 MPaG or more and 10 MPaG or less (gauge pressure; the same shall apply herein), preferably at 1 MPaG or more and 6 MPaG or less, more preferably at 3 MPaG or more and 6 MPaG or less. If the pressure is 0.1 MPaG or more, the reflux of unreacted hydrogen fluoride facilitates raising the reaction temperature to a suitable level, which is practical. If the pressure is 10 MPaG or less, the fluorination of 1230xd can be performed in a general-purpose reactor, which is economical. However, these do not preclude the fluorination of 1230xd from being carried out at less than 0.1 MPaG or greater than 10 MPaG.

(Solvent)

In the fluorination of 1230xd in the liquid phase, the use of a solvent is not essential, and it is usually preferable not to use a solvent from the viewpoints of productivity and economics. On the other hand, the use of a solvent may be preferable from the viewpoints of homogeneity of the reaction and operability after the reaction. When a solvent is used, the type of the solvent is not particularly limited as long as the 1230xd raw material can be dissolved, but an organic solvent that has a boiling point higher than that of the target product and that is not fluorinated by hydrogen fluoride is preferable. Examples of such solvents include but are not limited to tetramethylene sulfone (sulfolane), perfluoroalkanes, perfluoroalkenes, hydrofluorocarbons, and the like. The amount of the solvent used is not particularly limited as long as the 1230xd raw material can be dissolved. For example, the amount of the solvent used is preferably 80 mass % or less for the 1230xd raw material (when 1231xd is included in the raw material, the 1230xd raw material means the total amount of 1230xd and 1231xd), and more preferably 40 mass % or less, but more than these may be used as desired.

(Catalyst)

A catalyst may be used in the fluorination of 1230xd in the liquid phase. However, the use of the catalyst is not essential. When the catalyst is used, the type of catalyst is, for example, Lewis acid catalyst containing metal such as tin, titanium (more specifically, tin chloride ($SnCl_4$), titanium chloride ($TiCl_4$), etc.). The amount of the catalyst used is, for example, 0.01 mol % or more and 20 mol % or less per the 1230xd raw material.

(Reactor)

In the fluorination of 1230xd in the liquid phase, the material of the reactor to be used is preferably one that is inert to the raw materials, solvents, and the components of the reaction solution containing the reaction products and the like, and that is acid resistant. Such materials include, for example, stainless steel (such as SUS304 and SUS316), Hastelloy™, Inconel™, Monel™, and the like. Such reactor is well known in the art.

(Example of Operation Procedure)

An example of procedures for operating the fluorination of 1230xd in the liquid phase is provided below but is not limited thereto. In batch operation or semi-continuous flow operation, for example, a predetermined amount of a predetermined raw material is introduced into the reactor, a predetermined amount of a solvent is introduced as desired, and a reaction is performed under predetermined conditions. When the catalyst is used, it is preferable to introduce the catalyst into the reactor in advance or together with a raw material or a solvent. The procedure for introducing the raw material into the reactor is not particularly limited. For example, 1230xd may be introduced into the reactor, after which hydrogen fluoride may be introduced into the reactor. At this time, if a solvent is introduced as desired, a part or all of the solvent may be introduced into the reactor prior to introducing hydrogen fluoride into the reactor, or may be introduced into the reactor at the same time as introducing hydrogen fluoride, or hydrogen fluoride and the solvent may be mixed and introduced into the reactor.

In continuous-flow operation, for example, 1230xd and hydrogen fluoride are separately introduced in predetermined amounts into the reactor, and the reaction is carried out under a predetermined condition. Optionally, the solvents used may be introduced into the reactor separately from the 1230xd and hydrogen fluoride, or as a 1230xd solution and/or a hydrogen fluoride solution.

(Purification)

The method of purifying the target product from the reaction product obtained by the fluorination of 1230xd is not particularly limited, and a known purification method can be employed. If necessary, the reaction products can be rinsed with water, alkaline washing and the like to remove chlorine and acid components that can be contained in the reaction products. Moisture in the reaction product may also be removed by a dehydration treatment or the like or may be combined with a treatment for removing chlorine components and acid components. Furthermore, operations such as distillation may be performed.

Hereinafter, examples of methods for purifying 1232xd and 1231xd from the reaction product obtained by fluorination of 1230xd will be described, but the present invention is not limited thereto. For example, high purity 1232xd or 1231xd can be obtained by flowing the reaction product through a cooled condenser to condense the reaction product, rinsing the reaction product with water or/and an alkaline solution to remove chlorine components, acid components, and the like from the reaction product, drying the reaction product with a desiccant such as zeolite or activated carbon and carrying out a normal distillation operation.

In one embodiment of the present invention, unreacted raw material 1230xd or hydrogen fluoride may be recovered and used to the fluorination of 1230xd. In one embodiment, 1231xd produced by fluorination of 1230xd may be recovered and used to the fluorination of 1230xd.

1232xd and 1231xd exist as a liquid at normal temperature and pressure.

Although the fluorination of 1230xd performed in the liquid phase has been described above, in one embodiment, the fluorination of 1230xd by hydrogen fluoride may be performed in a vapor phase.

<Fluorination of 1230xd in the Vapor Phase>

(Catalyst)

The fluorination reaction of 1230xd in the vapor phase can be carried out either in the presence or absence of a catalyst.

If the fluorination of 1230xd is carried out in the vapor phase in the presence of the catalyst, a metal catalyst can be used. The metal catalyst specifically includes at least one metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten. As the metal catalyst, a compound of the above metal is preferable, and an oxide, a halide, and an oxyhalide of the above metal are more preferable. The halogen of the halide may be any of iodine, bromine, chlorine, and fluorine. The metal catalyst is more preferably partial halide or total halide of the above metal, and particularly preferably partial fluoride or total fluoride of the above metal.

The metal catalyst may be a supported catalyst or an unsupported catalyst. The support of the supported catalyst is not particularly limited, but carbon, an oxide of the aforementioned metal, an oxyhalide (preferably an oxyfluoride), a halide (preferably a fluoride), or the like is preferably used. Among such supports, particularly preferred are activated carbon, oxides of at least one metal selected from aluminum, chromium, zirconium and titanium, oxyhalides (particularly preferably oxyfluorides), halides (particularly preferably fluorides). In the case of the supported catalyst, the supported material supported on the support is a compound of the aforementioned metal. For example, a halide (e.g., fluoride, chloride, fluoride chloride) of the aforementioned metal, an oxyhalide (e.g., oxyfluoride, oxychloride, oxyfluoride chloride), a nitrate, or the like is supported on the support. Such a metal compound may be supported alone, or two or more kinds may be supported together. Among the supported material, particularly preferred are halides and oxyhalides of at least one metal selected from aluminum, chromium, zirconium and titanium. Specific supported material includes chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper(II) chloride, zinc(II) chloride, lanthanum nitrate, tin tetrachloride, and the like. In the case where the support and the supported material are metal compounds, the support and the supported material are metal compounds different from each other.

The metallic catalyst is preferably used for the fluorination reaction of 1230xd after being subjected to fluorination treatment. The fluorination treatment of the metal catalyst is not particularly limited but is generally carried out by contacting the metal catalyst with a fluorination agent, such as hydrogen fluoride, fluorination hydrocarbon, or fluorination chlorinated hydrocarbon. The fluorination treatment is performed at a temperature of 200° C. or more, for example, although the temperature is not particularly limited. Although there is no particular upper limit to the fluorination treatment temperature, it is practically preferable to perform the treatment temperature at 600° C. or less. In this reaction, for example, $Al_2O_3$, $Cr_2O_3$, $Cr_2O_3/Al_2O_3$, $Cr_2O_3/AlF_3$, $Cr_2O_3/C$, $Ti_2O_3$, $Zr_2O_3$, $Zr_2O_3/Ti_2O_3$, $CoCl_2/Cr_2O_3/Al_2O_3$, $NiCl_2/Cr_2O_3/Al_2O$, $CoCl_2/AlF_3$, $NiCl_2/AlF_3$, $FeCl_3/C$, $SnCl_4/C$, $TaCl_5/C$, $SbCl_3/C$, $AlCl_3/C$, and $AlF_3/C$ which are fluorinated can be used.

In one embodiment, when it is desired to predominantly produce 1231 xd, the fluorination of 1230xd is preferably carried out in the absence of the catalyst.

(Filler)

The fluorination reaction of 1230xd in the vapor phase may be carried out in the presence or absence of fillers. Examples of the filler include carbon such as activated carbon, heat-resistant plastic, ceramics, and zero-valent metal such as stainless steel and the like. Among these, activated carbon is particularly preferable. For example, the reaction can be carried out in the presence of at least a filler selected from carbon, refractory plastics and ceramics.

(Temperature)

In the fluorination reaction of 1230xd in the vapor phase, the reaction temperature is not particularly limited as long as the target product can be produced. This reaction can be carried out at 100° C. or more, preferably at 170° C. or more, and more preferably at 220° C. or more. This reaction also can be carried out at 500° C. or less, preferably at 480° C.

or less, and more preferably at 430° C. or less. For example, the reaction can be performed at 100° C. or more and 500° C. or less, preferably 170° C. or more and 480° C. or less, and more preferably 220° C. or more and 430° C. or less.
(Pressure)

In the fluorination reaction of 1230xd in the vapor phase, the reaction pressure is not particularly limited. The reaction may be carried out under reduced pressure, normal pressure (atmospheric pressure) or under pressure. This reaction can be carried out at a pressure of 0.01 MPaG or more and 10 MPaG or less (meaning gauge pressure; the same shall apply hereinafter), and the reaction is preferably carried out at a pressure of 0.01 MPaG or more and 1 MPaG or less, and atmospheric pressure is more preferable in order to prevent liquefaction of raw materials and products. Exceeding 10 MPaG is economically undesirable because it increases the cost of the pressure resistance design of the reactor.
(Contact Time)

For the vapor phase flow reaction, productivity is often discussed as the value (sec) obtained by dividing in which the volume A (mL) of the reaction zone by the feed rate B (mL/sec) of the raw material, which is referred to as the contact time. When the reaction zone is equipped with the catalyst, the apparent volume of the catalyst (mL) is considered to be above A. The value of B indicates the "volume of material gas introduced into the reactor per second", in this case the value of B is calculated from the number of moles of the material gas, pressure and temperature, assuming that the material gas is an ideal gas. In the reactor, by-products of compounds other than raw materials and target products and changes in the number of moles may occur but are not taken into account when calculating the "contact time".

The determination of the contact time depends on the raw materials used in the reaction, the reaction temperature, the type of the catalyst, and the like. Therefore, it is desirable to appropriately adjust the feed rate of the raw material for each of the raw material, the set temperature of the reactor, and the type of the catalyst to optimize the contact time.

In the fluorination of 1230xd, the contacting time can be 0.1 seconds or more and 300 seconds or less, preferably 5 seconds or more and 150 seconds or less, more preferably 10 seconds or more and 100 seconds or less. The contact time may be appropriately changed in accordance with the reaction pressure.
(Reactor)

In the fluorination reaction of 1230xd in the vapor phase, the reactor is not particularly limited, but it is preferable to use a reactor suitable for the vapor phase reaction. The reactor is preferably formed of a material having heat resistance and acid resistance, and may be formed of, for example, stainless steel, Hastelloy™, Monel™, platinum, nickel, carbon, fluorine resin, or a material lined with these materials, but is not limited thereto.

In this reaction, inert gas such as nitrogen, argon, or helium, or an oxidizing gas such as chlorine, oxygen, or air may be supplied to the reactor in order to suppress a side reaction or to maintain or improve the activity of the metal catalyst. Such gas may be supplied to the reactor alone or may be supplied to the reaction system together with the reaction raw material. Such gas may be alone or mixed gas. The feed amount to the reactor is not particularly limited, but is preferably 0.0001 mol % or more and 200 mol % or less, more preferably 0.001 mol % or more and 100 mol % or less, and particularly preferably 0.1 mol % or more and 10 mol % or less with respect to the reaction material.

(Example of Operation Procedure)

An example of procedures of the fluorination reaction of 1230xd in the vapor phase is shown below. The reaction material is introduced into the reactor, and the vapor phase reaction is carried out under the above-mentioned conditions. The raw material is preferably gaseous when introduced into the reactor, and if necessary, the raw material is gasified by a vaporizer and introduced into the reactor. When the catalyst is used, it is preferable to equip the reactor with the catalyst beforehand.

The method of purifying the target product from the reaction product obtained by this reaction is not particularly limited. If necessary, removal treatment of chlorine components, acid components, and the like which may be contained in the reaction product may be performed. Dehydration treatment or the like may be performed to remove moisture, or the dehydration treatment may be performed in combination with the treatment to remove chlorine components or acid components. For example, the reaction product can be condensed by flowing through a cooled condenser, rinsed with water or/and an alkaline solution to remove chlorine components, acid components, and the like, dried with a desiccant such as zeolite, activated carbon, and the like, and then subjected to a distillation operation to obtain an object of high purity.

As explained above, the fluorination of 1230xd can be carried out not only in the liquid phase but also in the vapor phase.

<Fluorination of 1231xd>

In one embodiment of the present invention, hydrogen fluoride is used as a fluorination agent to fluorinate 1231xd. Fluorination of 1231xd can be done according to the above fluorination condition of 1230xd. Thus, it is possible to produce 1232xd.

In one embodiment, 1231xd may be produced by fluorination of 1230xd and then 1232xd may be produced by fluorination of 1231xd.

<Producing Method of 1230xd>

[Dehydrochlorination Process of 240 da].

As described above, 1230xd is a known compound and can be produced by various methods, but by adopting the following 1230xd production method, 1230xd can be produced efficiently using 1,1,2,3,3-pentachloropropane (hereinafter also referred to as 240 da) as a starting material.

1230xd can be produced in the liquid phase by a process of dehydrochlorination of 240 da in the presence of an aqueous solution of an inorganic base (hereinafter this process may be referred to as the "240 da dehydrochlorination process").

(240 da)

240 da is a known compound and can be produced by various methods but can be efficiently produced by the "alkylation process" described later. This does not preclude the production of 240 da by other methods.

(Aqueous Solution of Inorganic Base)

In the dehydrochlorination process of 240 da, there is no particular limitation on an inorganic base as long as it can dehydrochlorination 240 da. Specific examples include alkali metal hydroxides or alkaline earth metal hydroxides, and among these, at least one selected from the group consisting of lithium hydroxide, sodium hydroxide, potassium hydroxide, magnesium hydroxide and calcium hydroxide is preferable.

The amount of the inorganic base used is not particularly limited. Generally, the amount is 1 equivalent or more to 240 da. The upper limit is not particularly limited, but is usually 10 equivalents or less, preferably 5 equivalents or less, more preferably 3 equivalents or less, and particularly preferably 2 equivalents.

The inorganic base concentration of the inorganic base in aqueous solution is not particularly limited. Generally, the content is 5 mass % or more, preferably 10 mass %. The upper limit is not particularly limited but is generally 40 mass % or less, preferably 30 mass %.

In one embodiment, the concentration of the inorganic base in aqueous solution of the inorganic base is, for example, 5 mass % or more and 40 mass % or less, 5 mass % or more and 30 mass % or less, 10 mass % or more and 40 mass % or less, or 10 mass % or more and 30 mass % or less.

In one embodiment, the concentration of the inorganic base in aqueous solution of the inorganic base is 5 mass % or more and 40 mass % or less, preferably 10 mass % or more and 30 mass % or less.

When a phase transfer catalyst described later is used, aqueous solution of the inorganic base and the phase transfer catalyst may be supplied to the reactor in separate streams but are preferably mixed in advance.

(Phase Transfer Catalyst)

The dehydrochlorination process of 240 da is preferably carried out in the presence of the phase transfer catalyst. As such the phase transfer catalyst, water-soluble organic substances such as alcohols, ethers, ketones, amide compounds, and the like, or amine salts can be used. These phase transfer catalysts may be of one type or two or more types.

Examples of alcohols used as the phase transfer catalyst include alcohols having 1 to 4 carbon atoms.

The ethers used as the phase transfer catalyst include, for example, 18-crown-6-ether and the like.

The ketones used as the phase transfer catalyst include, for example, acetone, ethyl methyl ketone, and the like.

Examples of amide compounds used as the phase transfer catalyst include DMF, DMAc, and the like.

Examples of the amine salt used as the phase transfer catalyst include tetrabutylammonium salt, trioctylmethylammonium salt, benzyldimethyloctadecylammonium salt, and the like.

Among them, alcohols having 1 to 4 carbon atoms, 18-crown-6-ether, acetone, and ethyl methyl ketone are preferable as the phase transfer catalyst.

The amount of the phase transfer catalyst used is not particularly limited as long as the effect as the phase transfer catalyst can be obtained. Generally, the amount of the phase transfer catalyst used with respect to 240 da is 0.01 mass % or more, preferably 0.1 mass % or more. The upper limit is not particularly limited but is generally 40 mass % or less, preferably 20 mass % or less, more preferably 10 mass % or less.

In one embodiment, the amount of the phase transfer catalyst may be, for example, 0.01 mass % or more and 40 mass % or less, 0.01 mass % or more and 20 mass % or less, 0.01 mass % or more and 10 mass % or less, 0.01 mass % or more and 0.1 mass % or less, 0.1 mass % or more and 40 mass % or less, 0.1 mass % or more and 20 mass % or less, or 0.1 mass % or more and 10 mass % or less for 240 da.

In one embodiment, the amount of the phase transfer catalyst used is 0.01 mass % or more and 40 mass % or less, preferably 0.1 mass % or more and 20 mass % or less, for 240 da.

(Temperature)

In the 240 da dehydrochlorination process, the temperature is not particularly limited as long as the target product can be produced under a liquid phase condition. Generally, it is carried out at 0° C. or more, preferably at 5° C. or more, more preferably at 10° C. or more. The upper limit is not particularly limited, but is generally 150° C. or less, preferably 100° C. or less, more preferably 60° C. or less.

In one embodiment, the 240 da dehydrochlorination process is performed, for example, at 0° C. or more and 150° C. or less, 0° C. or more and 100° C. or less, 0° C. or more and 60° C. or less, 5° C. or more and 150° C. or less, 5° C. or more and 100° C. or less, 5° C. or more and 60° C. or less, 10° C. or more and 150° C. or less, 10° C. or more and 100° C. or less, 10° C. or more and 60° C. or less, 60° C. or more and 150° C. or less, or 60° C. or more and 100° C. or less.

In one embodiment, the 240 da dehydrochlorination process is performed at 0° C. or more and 150° C. or less, preferably 5° C. or more and 100° C. or less, more preferably 10° C. or more and 60° C. or less.

(Pressure)

In the 240 da dehydrochlorination process, the pressure is not particularly limited as long as the target product can be produced under a liquid phase condition. Generally, the pressure in the 240 da dehydrochlorination process is preferably equal to or higher than atmospheric pressure and equal to or lower than 10 MPaG, and more preferably equal to or higher than atmospheric pressure and equal to or lower than 1 MPaG. To reduce the cost of the reactor, the pressure in the 240 da dehydrochlorination process is most preferably atmospheric pressure.

(Solvent)

In the dehydrochlorination process, the use of solvents is not essential. This does not prevent the dehydrochlorination process from being carried out in the presence of a solvent, but when a solvent is used, it is preferable to use a solvent which does not adversely affect the reaction.

(Reaction Method)

The dehydrochlorination process may be performed by any of batch type, semi-continuous flow type, and continuous flow methods.

(Reactor)

In the dehydrochlorination process, the material of the reactor is not particularly limited. A material having base resistance is preferable. Specifically, a reactor made of glass or stainless steel is preferable. A reactor lined with glass or resin is also preferred. Further, it is preferable that the reactor is provided with various equipments such as a stirring equipment and a reflux tower.

In the case where the dehydrochlorination process and the alkylation process described later are performed in the same reactor, it is preferable to provide an introduction pipe into which the liquid can flow.

(Example of Operation Procedure)

An example of the operating procedure of the dehydrochlorination process is described below but is not limited thereto. The phase transfer catalyst and 240 da are charged to a reactor equipped with a reflux column through which a refrigerant (e.g., water) is flowed. An aqueous solution of the inorganic base is flowed into a liquid inflow pipe, and the reaction is carried out under a predetermined condition. The reaction is terminated when it is observed that 240 da is nearly consumed by gas chromatographic analysis or the like of the sampled reactants.

(Purification)

The 1230xd obtained can be purified by a general purification operation. For example, raw materials and the like can be easily separated from 1230xd by an operation such as distillation, preferably vacuum distillation.

[Alkylation Process]

240 da can be efficiently produced by reacting 1,2-dichloroethylene with chloroform in the presence of Lewis acid catalyst (hereinafter this process may be referred to as "alkylation process").

(Raw Materials)

The amounts of 1,2-dichloroethylene and chloroform used in the alkylation process is not particularly limited as long as 240 da can be produced. Generally, 1 mol or more of chloroform is used for 1 mol of 1,2-dichloroethylene, or 1 mol of 1,2-dichloroethylene is used for 1 mol of chloroform.

In one embodiment, chloroform is used in excess of stoichiometric amounts for 1,2-dichloroethylene. Thereby, by-products such as heptachloropentane can be suppressed. Specifically, chloroform is used in an amount of more than 1 mol, preferably 2 mol or more, more preferably 3 mol or more per 1 mol of 1,2-dichloroethylene. The upper limit is not particularly limited, but chloroform is used in an amount of 20 mol or less, preferably 10 mol or less for 1 mol of 1,2-dichloroethylene from the viewpoint of economical production.

In the alkylation process, heptachloropentane is a type of alkylated compound of 240 da, and by-products are produced as the existence ratio of 240 da in the reaction system increases. Therefore, in the reaction system, if chloroform as a raw material is present more than 1,2-dichloroethylene, by-production of heptachloropentane can be suppressed.

(Lewis Acid Catalyst)

In the alkylation process, a metal halide can be used as Lewis acid catalyst. Here, the metal halide refers to a compound having a bond between a metal atom and a halogen atom. The bonding of metal atoms-halogen atoms can be confirmed by infrared spectroscopy (IR method), X-ray diffraction method (XRD method), X-ray photoelectron spectroscopy (XPS method), etc. Specifically, such a metal halide is preferably a metal halide of at least one metal selected from the group consisting of aluminum, vanadium, chromium, manganese, iron, cobalt, nickel, copper, zirconium, niobium, molybdenum, ruthenium, rhodium, palladium, silver, tin, antimony, tantalum, and tungsten. The metal halide may be a fluoride, a chloride, a bromide, or an iodide of the above metals, and among these, a chloride of the above metals is preferable. In some embodiments, the chloride of at least one metal selected from the group consisting of aluminium, iron, tin and antimony is particularly preferred as Lewis acid catalyst. Among these, aluminum chloride and iron chloride are more preferable, and ferric chloride is preferable for iron chloride.

The use of anhydrous Lewis acid catalyst is preferred because it is highly catalytically active. Commercial anhydrides of Lewis acid catalyst may be used as is, or hydrates may be treated with a dehydrating agent such as thionyl chloride to obtain anhydrides.

When a chloride of the above metal is used as Lewis acid catalyst, nitrate, carbonate, or the like of the above metal or a zero-valent metal powder can be derived to the chloride of the metal by hydrochlorination in advance. Therefore, nitrate, carbonate, or the like of the above metals, and zero-valent metal powders treated with hydrochloric acid can also be used as Lewis acid catalyst.

Since the chloroform raw material in the alkylation process is effective to activate and/or chlorinate the zero-valent metal, Lewis acid catalyst may be a zero-valent metal powder.

In the alkylation process, the amount of Lewis acid catalyst used is not particularly limited as long as it is an effective amount as the catalyst. The optimum amount varies depending on the type of catalysts and operating conditions such as the reaction temperatures, but generally, the amount of Lewis acid catalyst used is 0.01 mass % or more, preferably 0.1 mass % or more for 1,2-dichloroethylene raw material. The upper limit is not particularly limited but is generally 40 mass % or less, preferably 20 mass % or less.

In one embodiment, the amount of Lewis acid catalyst used may be 0.01 mass % or more and 40 mass % or less, 0.01 mass % or more and 20 mass % or less, 0.1 mass % or more and 40 mass % or less, or 0.1 mass % or more and 20 mass % or less for 1,2-dichloroethylene.

In one embodiment, the amount of Lewis acid catalyst used is 0.01 mass % or more and 40 mass % or less, preferably 0.1 mass % or more and 20 mass % or less for 1,2-dichloroethylene. In this range, the reaction proceeds at a good reaction rate, and an unexpected side reaction is unlikely to occur.

(Temperature)

In the alkylation process, temperature is not particularly limited as long as the target product can be produced under a liquid phase condition. Generally, it is carried out at 0° C. or more, preferably at 20° C. or more, more preferably at 40° C. or more. The upper limit is not particularly limited, but is generally 100° C. or less, preferably 80° C. or less, more preferably 70° C. or less.

In one embodiment, the alkylation process is performed at temperature of 0° C. or more and 100° C. or less, 0° C. or more and 80° C. or less, 0° C. or more and 70° C. or less, 20° C. or more and 100° C. or less, 20° C. or more and 80° C. or less, 20° C. or more and 70° C. or less, 40° C. or more and 100° C. or less, 40° C. or more and 80° C. or less, or 40° C. or more and 70° C. or less.

In some embodiments, the alkylation process is performed at 0° C. or more and 100° C. or less, preferably 20° C. or more and 80° C. or less, more preferably 20° C. or more and 70° C. or less.

(Pressure)

In the alkylation process, the pressure is not particularly limited as long as the target product can be produced under a liquid phase condition. Generally, the alkylation process is performed at 0 MPaG or more and 1 MPaG or less, preferably at 0 MPaG or more and 0.5 MPaG or less, and particularly preferably at atmospheric pressure.

(Solvent)

In the alkylation process, the use of a solvent is not essential. This does not prevent the alkylation process from being carried out in the presence of a solvent, but in the case of using a solvent, it is preferable to adopt a solvent which does not adversely affect the reaction.

(Reaction Method)

The alkylation process may be carried out in any method of a batch type, semi-continuous flow type, and continuous flow type. Since Lewis acid catalyst is used in the alkylation process, it is preferable that moisture is as small as possible. In one embodiment, the water content is preferably kept at 1 mass % or less, more preferably at 0.1 mass % or less for the total mass of the reaction material.

(Reactor)

In the alkylation process, the material of the reactor is not particularly limited. A reactor made of glass or stainless steel is preferred because chlorine gas or hydrogen chloride gas may be byproducts, albeit in trace amounts. A reactor lined with glass or resin is also preferred. It is preferable that the reactor be provided with various equipments such as a liquid introducing pipe, a stirring equipment, and a reflux tower.

(Example of Operation Procedure)

An example of the operating procedure of the alkylation process is described below but is not limited thereto. Lewis acid catalyst and chloroform are charged to a reactor equipped with a refluxing column through which a coolant (e.g., water) is flowed. Seal with inert gas as necessary. 1,2-dichloroethylene is flowed into the liquid inflow pipe, and the reaction is carried out under predetermined conditions. The reaction is terminated when it is observed that 1,2-dichloroethylene is almost consumed by gas chromatographic analysis or the like of the sampled reactants.

After completion of the reaction, acid aqueous solution is added to the reaction product. As the acidic aqueous solution, for example, aqueous solution of at least one acid selected from the group consisting of hydrogen fluoride, hydrogen chloride, hydrogen bromide, hydrogen iodide, formic acid, acetic acid, monofluoroacetic acid, difluoroacetic acid, trifluoroacetic acid, chlorodifluoroacetic acid, trichloroacetic acid, sulfuric acid, and nitric acid is used.

(Purification)

The resulting 240 da can be purified by conventional purification procedures. For example, raw materials and by-products can be easily separated from 240 da by operation such as distillation, preferably vacuum distillation. The separated raw material may be reused as a raw material for the alkylation process.

The obtained 240 da may be used as a raw material in the above-mentioned dehydrochlorination process without performing post-treatment such as separating of Lewis acid catalyst and distilling purification. This does not preclude post-processing.

<Solvent Composition>

[1232xd]

The solvent composition of the present invention includes at least 1232xd. The content of 1232xd is not particularly limited, but in one embodiment, 1232xd is included in 20 mass % or more for the total amount of the solvent composition of the present invention. In another embodiment, 1232xd is included at 30 mass % or more for the total amount of the solvent composition of the present invention. In another embodiment, 1232xd is included in 40 mass % or more for the total amount of the solvent composition of the present invention. In yet another embodiment, 1232xd is included in an amount of 50 mass % or more for the total amount of the solvent composition of the present invention. In yet another embodiment, 1232xd is included in an amount of 60 mass % or more for the total amount of the solvent composition of the present invention. In yet another embodiment, 1232xd is included in an amount of 70 mass % or more for the total amount of the solvent composition of the present invention. In yet another embodiment, 1232xd is included in an amount of 80 mass % or more for the total amount of the solvent composition of the present invention. In yet another embodiment, 1232xd is included in an amount of 90 mass % or more for the total amount of the solvent composition of the present invention. In yet another embodiment, 1232xd is included an amount of 95 mass % or more for the total amount of the solvent composition of the present invention. In yet another embodiment, 1232xd is included an amount of 97 mass % or more for the total amount of solvent composition of the present invention. In yet another embodiment, 1232xd is included 98 mass % or more for the total amount of the solvent composition of the present invention. In yet another embodiment, 1232xd is included 99 mass % or more for the total amount of the solvent composition of the present invention. In yet another embodiment, the solvent composition of the present invention consists only of 1232xd.

In the solvent composition of the present invention, the content of 1232xd may be 20 mass % or more and 99 mass % or less, 20 mass % or more and 98 mass % or less, 20 mass % or more and 97 mass % or less, 20 mass % or more and 95 mass % or less, 20 mass % or more and 90 mass % or less, 20 mass % or more and 80 mass % or less, 20 mass % or more and 70 mass % or less, 20 mass % or more and 60 mass % or less, 20 mass % or more and 50 mass % or less, 20 mass % or more and 40 mass % or less, 20 mass % or more and 30 mass % or less, 30 mass % or more and 99 mass % or less, 30 mass % or more and 98 mass % or less, 30 mass % or more and 97 mass % or less, 30 mass % or more and 95 mass % or less, 30 mass % or more and 90 mass % or less, 30 mass % or more and 80 mass % or less, 30 mass % or more and 70 mass % or less, 30 mass % or more and 60 mass % or less, 30 mass % or more and 50 mass % or less, 30 mass % or more and 40 mass % or less, 40 mass % or more and 99 mass % or less, 40 mass % or more and 98 mass % or less, 40 mass % or more and 97 mass % or less, 40 mass % or more and 95 mass % or less, 40 mass % or more and 90 mass % or less, 40 mass % or more and 80 mass % or less, 40 mass % or more and 70 mass % or less, 40 mass % or more and 60 mass % or less, 40 mass % or more and 50 mass % or less, 50 mass % or more and 99 mass % or less, 50 mass % or more and 98 mass % or less, 50 mass % or more and 97 mass % or less, 50 mass % or more and 95 mass % or less, 50 mass % or more and 90 mass % or less, 50 mass % or more and 80 mass % or less, 50 mass % or more and 70 mass % or less, 50 mass % or more and 60 mass % or less, 60 mass % or more and 99 mass % or less, 60 mass % or more and 98 mass % or less, 60 mass % or more and 97 mass % or less, 60 mass % or more and 95 mass % or less, 60 mass % or more and 90 mass % or less, 60 mass % or more and 80 mass % or less, 60 mass % or more and 70 mass % or less, 70 mass % or more and 99 mass % or less, 70 mass % or more and 98 mass % or less, 70 mass % or more and 97 mass % or less, 70 mass % or more and 95 mass % or less, 70 mass % or more and 90 mass % or less, 70 mass % or more and 80 mass % or less, 80 mass % or more and 99 mass % or less, 80 mass % or more and 98 mass % or less, 80 mass % or more and 97 mass % or less, 80 mass % or more and 95 mass % or less, 80 mass % or more and 90 mass % or less, 90 mass % or more and 99 mass % or less, 90 mass % or more and 98 mass % or less, 90 mass % or more and 97 mass % or less, 90 mass % or more and 95 mass % or less, 95 mass % or more and 99 mass % or less, 95 mass % or more and 98 mass % or less, 95 mass % or more and 97 mass % or less, 97 mass % or more and 99 mass % or less, 97 mass % or more and 98 mass % or less, 98 mass % or more and 99 mass % or less, or 100 mass %, for the total amount of the solvent composition of the present invention.

Since 1232xd is olefin having a double bond between carbon atoms, it has a short lifetime in the air and a low global warming potential (GWP). Since 1232xd does not have a flash point, the risk of ignition and fire etc. in the use environment is low.

In one embodiment of the present invention, 1232xd consists only of the cis isomer (1232xd(Z)).

In another embodiment of the present invention, 1232xd consists of a mixture of the cis isomer (1232xd(Z)) and the trans isomer (1232xd(E)). In the mixture of 1232xd(Z) and 1232xd(E), the composition is not particularly limited, but may be the following molar ratio.

1232xd(Z):1232xd(E)=0.01~99.99:99.99~0.01
1232xd(Z):1232xd(E)=50.00~99.99:50.00~0.01
1232xd(Z):1232xd(E)=60.00~99.99:40.00~0.01
1232xd(Z):1232xd(E)=70.00~99.99:30.00~0.01
1232xd(Z):1232xd(E)=80.00~99.99:20.00~0.01
1232xd(Z):1232xd(E)=90.00~99.99:10.00~0.01

In yet another embodiment of the present invention, 1232xd consists only of the trans isomer (1232xd(E)).

[1231xd]

The solvent composition of the present invention may include 1231xd along with 1232xd. In one embodiment, solvent composition containing 1232xd and 1231xd has excellent cleaning performance. When the solvent composition of the present invention contains 1231xd, the lower limit of the content thereof is 0.001 mass % or more in one embodiment, 0.01 mass % or more in another embodiment, 0.1 mass % or more in another embodiment, 1 mass % or more in another embodiment, 3 mass % or more in another embodiment, 5 mass % or more in another embodiment, and 10 mass % or more in another embodiment, for the total amount of solvent composition of the present invention. The upper limit of the content of 1231xd is 40 mass % or less in one embodiment, 25 mass % or less in another embodiment, and 15 mass % or less in another embodiment, for the total amount of the solvent composition of the present invention.

In the solvent composition of the present invention, the content of 1231xd may be 0.001 mass % or more and 40 mass % or less, 0.001 mass % or more and 25 mass % or less, 0.001 mass % or more and 15 mass % or less, 0.001 mass % or more and 10 mass % or less, 0.001 mass % or more and 5 mass % or less, 0.001 mass % or more and 3 mass % or less, 0.001 mass % or more and 1 mass % or less, 0.001 mass % or more and 0.1 mass % or less, 0.001 mass % or more and 0.01 mass % or less, 0.01 mass % or more and 40 mass % or less, 0.01 mass % or more and 25 mass % or less, 0.01 mass % or more and 15 mass % or less, 0.01 mass % or more and 10 mass % or less, 0.01 mass % or more and 5 mass % or less, 0.01 mass % or more and 3 mass % or less, 0.01 mass % or more and 1 mass % or less, 0.01 mass % or more and 0.1 mass % or less, 0.1 mass % or more and 40 mass % or less, 0.1 mass % or more and 25 mass % or less, 0.1 mass % or more and 15 mass % or less, 0.1 mass % or more and 10 mass % or less, 0.1 mass % or more and 5 mass % or less, 0.1 mass % or more and 3 mass % or less, 0.1 mass % or more and 1 mass % or less, 1 mass % or more and 40 mass % or less, 1 mass % or more and 25 mass % or less, 1 mass % or more and 15 mass % or less, 1 mass % or more and 10 mass % or less, 1 mass % or more and 5 mass % or less, 1 mass % or more and 3 mass % or less, 3 mass % or more and 40 mass % or less, 3 mass % or more and 25 mass % or less, 3 mass % or more and 15 mass % or less, 3 mass % or more and 10 mass % or less, 3 mass % or more and 5 mass % or less, 5 mass % or more and 40 mass % or less, 5 mass % or more and 25 mass % or less, 5 mass % or more and 15 mass % or less, 5 mass % or more and 10 mass % or less, 10 mass % or more and 40 mass % or less, 10 mass % or more and 25 mass % or less, 10 mass % or more and 15 mass % or less, 15 mass % or more and 40 mass % or less, 15 mass % or more and 25 mass % or less, or 25 mass % or more and 40 mass % or less, for the total amount of the solvent composition of the present invention.

Since 1231xd is olefin having a double bond between carbon atoms, it has a short lifetime in the air and a low global warming potential (GWP). Since 1231xd does not have a flash point, the risk of ignition and fire etc. in the use environment is low.

[Organic Compound (A)]

The solvent composition of the present invention may include another organic compound (A) along with 1232xd or with 1232xd and 1231xd.

If the solvent composition of the present invention includes the organic compound (A), the lower limit of the content, for the total amount of the solvent composition of the present invention, 0.01 mass % or more in one embodiment, 0.1 mass % or more in another embodiment, 1 mass % or more in another embodiment, 3 mass % or more in another embodiment, 5 mass % or more in another embodiment, 10 mass % or more in another embodiment. The upper limit of the content of the organic compound (A) is 80 mass % or less in one embodiment, 70 mass % or less in another embodiment, 60 mass % or less in another embodiment, 50 mass % or less in another embodiment, 40 mass % or less in another embodiment, 30 mass % or less in another embodiment, and 20 mass % or less in another embodiment, for the total amount of the solvent composition of the present invention.

In the solvent composition of the present invention, the content of the organic compound (A) may be 0.01 mass % or more and 80 mass % or less, 0.01 mass % or more and 70 mass % or less, 0.01 mass % or more and 60 mass % or less, 0.01 mass % or more and 50 mass % or less, 0.01 mass % or more and 40 mass % or less, 0.01 mass % or more and 30 mass % or less, 0.01 mass % or more and 20 mass % or less, 0.01 mass % or more and 10 mass % or less, 0.01 mass % or more and 5 mass % or less, 0.01 mass % or more and 3 mass % or less, 0.01 mass % or more and 1 mass % or less, 0.01 mass % or more and 0.1 mass % or less, 0.1 mass % or more and 80 mass % or less, 0.1 mass % or more and 70 mass % or less, 0.1 mass % or more and 60 mass % or less, 0.1 mass % or more 50 mass % or less, 0.1 mass % or more and 40 mass % or less, 0.1 mass % or more and 30 mass % or less, 0.1 mass % or more and 20 mass % or less, 0.1 mass % or more and 10 mass % or less, 0.1 mass % or more and 5 mass % or less, 0.1 mass % or more and 3 mass % or less, 0.1 mass % or more and 1 mass % or less, 1 mass % or more and 80 mass % or less, 1 mass % or more and 70 mass % or less, 1 mass % or more and 60 mass % or less, 1 mass % or more and 50 mass % or less, 1 mass % or more and 40 mass % or less, 1 mass % or more and 30 mass % or less, 1 mass % or more and 20 mass % or less, 1 mass % or more and 10 mass % or less, 1 mass % or more and 5 mass % or less, 1 mass % or more and 3 mass % or less, 3 mass % or more and 80 mass % or less, 3 mass % or more and 70 mass % or less, 3 mass % or more and 60 mass % or less, 3 mass % or more and 50 mass % or less, 3 mass % or more and 40 mass % or less, 3 mass % or more and 30 mass % or less, 3 mass % or more and 20 mass % or less, 3 mass % or more and 10 mass % or less, 3 mass % or more and 5 mass % or less, 5 mass % or more and 80 mass % or less, 5 mass % or more and 70 mass % or less, 5 mass % or more and 60 mass % or less, 5 mass % or more and 50 mass % or less, 5 mass % or more and 40 mass % or less, 5 mass % or more and 30 mass % or less, 5 mass % or more and 20 mass % or less, 5 mass % or more and 10 mass % or less, 10 mass % or more and 80 mass % or less, 10 mass % or more and 70 mass % or less, 10 mass % or more and 60 mass % or less, 10 mass % or more and 50 mass % or less, 10 mass % or more and 40 mass % or less, 10 mass % or more and 30 mass % or less, 10 mass % or more and 20 mass % or less, 20 mass % or more and 80 mass % or less, 20 mass % or more and 70 mass % or less, 20 mass % or more and 60 mass % or less, 20 mass % or more and 50 mass % or less, 20 mass % or more and 40 mass % or less, 20 mass % or more and 30 mass % or less, 30 mass % or more and 80 mass % or less, 30 mass % or more and 70 mass % or less, 30 mass % or more and 60 mass % or less, 30 mass % or more and 50 mass % or less, 30 mass % or more and 40 mass % or less, 40 mass % or more and 80 mass % or less, 40 mass % or more and 70 mass % or less, 40 mass % or more and 60 mass % or less, 40 mass % or more and 50 mass % or less, 50 mass % or more and 80 mass % or less, 50 mass % or more and 70 mass % or less, 50 mass % or more and 60 mass % or less, 60 mass % or more and 80 mass % or less, 60 mass % or more and 70 mass % or less, or 70 mass % or more and 80 mass % or less, for the total amount of the solvent composition of the present invention.

Examples of the organic compound (A) include hydrocarbons, alcohols, ketones, ethers, esters, chlorocarbons, HFCs, HFEs, and the like. The organic compound (A) may be one kind or two or more kinds.

As the hydrocarbons used as the organic compound (A), hydrocarbons having 5 or more carbon atoms are preferable. The hydrocarbons may be chain, cyclic, saturated hydrocarbons, or unsaturated hydrocarbons. Specific examples of the hydrocarbons include n-pentane, 2-methylbutane, n-hexane, 2-methylpentane, 2,2-dimethylbutane, 2,3-dimethylbutane, n-heptane, 2-methylhexane, 3-methylhexane, 2,4-dimethylpentane, n-octane, 2-methylheptane, 3-methylheptane, 4-methylheptane, 2,2-dimethylhexane, 2,5-dimethylhexane, 3,3-dimethylhexane, 2-methl-3-ethylpentane, 3-methyl-3-ethylpentane, 2,3,3-trimethylpentane, 2,3,4-trimethylpentane, 2,2,3-trimethylpentane, 2-methylheptane, 2,2,4-trimethylpentane, n-nonane, 2,2,5-trimethylhexane, n-decane, n-dodecane, 2-methyl-2-butene, 1-pentene, 2-pentene, 1-hexene, 1-octene, 1-nonene, 1-decene, cyclopentane, methylcyclopentane, cyclohexane, methylcyclohexane, ethylcyclohexane, bicyclohexane, cyclohexene, α-pinene, dipentene, decalin, tetralin, amylnaphthalene, and the like. Among these, n-pentane, cyclopentane, n-hexane, cyclohexane, and n-heptane are preferable.

As the alcohols used as the organic compound (A), alcohols having 1 to 16 carbons are preferable. The alcohols may be chain, cyclic, saturated alcohols, or unsaturated alcohols. Specific examples of the alcohols include methanol, ethanol, n-propyl alcohol, isopropyl alcohol, n-butyl alcohol, sec-butyl alcohol, isobutyl alcohol, tert-butyl alcohol, 1-pentanol, 2-pentanol, 1-ethyl-1-propanol, 2-methyl-1-butanol, 3-methyl-1-butanol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, α-terpineol, 2,6-dimethyl-4-heptanol, nonyl alcohol, tetradecyl alcohol, and the like. Among these, methanol, ethanol, n-propyl alcohol, and isopropyl alcohol are preferable.

As the ketones used as the organic compound (A), ketones having 3 to 9 carbon atoms are preferable. The ketones may be chain, cyclic, saturated ketones or unsaturated ketones. The ketones include acetone, methyl ethyl ketone, 2-pentanone, 3-pentanone, 2-hexanone, methyl isobutyl ketone, 2-heptanone, 3-heptanone, 4-heptanone, diisobutyl ketone, mesityl oxide, phorone, 2-octanone, cyclohexanone, methylcyclohexanone, isophorone, 2,4-pentanedione, 2,5-hexanedione, diacetone alcohol, acetophenone, and the like. Among them, acetone and methyl ethyl ketone are preferable.

As the ethers used as the organic compound (A), ethers having 2 to 8 carbons are preferable. The ethers may be chain, cyclic, saturated ethers, or unsaturated ethers. Specific examples of the ethers include diethyl ether, dipropyl ether, diisopropyl ether, dibutyl ether, ethyl vinyl ether, butyl vinyl ether, anisole, phenetole, methyl anisole, furan, methyl furan, tetrahydrofuran, and the like. Among these, diethyl ether, diisopropyl ether and tetrahydrofuran are preferable.

As the esters used as the organic compound (A), esters having 2 to 19 carbons are preferable. The esters may be chain, cyclic, saturated esters, or unsaturated esters. Specific examples of the esters include methyl formate, ethyl formate, propyl formate, butyl formate, isobutyl formate, pentyl formate, methyl acetate, ethyl acetate, propyl acetate, isopropyl acetate, butyl acetate, isobutyl acetate, sec-butyl acetate, pentyl acetate, methoxybutyl acetate, sec-hexyl acetate, 2-ethylbutyl acetate, 2-ethylhexyl acetate, cyclohexyl acetate, benzyl acetate, methyl propionate, ethyl propionate, butyl propionate, methyl butyrate, ethyl butyrate, butyl butyrate, isobutyl butyrate, 2-hydroxy-2-methylpropionic acid ethyl, methyl benzoate, ethyl benzoate, propyl benzoate, butyl benzoate, benzyl benzoate, γ-butyrolactone, diethyl oxalate, dibutyl oxalate, dipentyl oxalate, diethyl malonate, dimethyl maleate, diethyl maleate, dibutyl maleate, dibutyl tartrate, tributyl citrate, dibutyl sebacate, dimethyl phthalate, diethyl phthalate, and dibutyl phthalate. Among them, methyl acetate and ethyl acetate are preferable.

As the chlorocarbons used as the organic compound (A), chlorocarbons having 1 to 3 carbon atoms are preferable. The chlorocarbons may be chain, cyclic, saturated chlorocarbons, or unsaturated chlorocarbons. Specific examples of chlorocarbons include methylene chloride, 1,1-dichloroethane, 1,2-dichloroethane, 1,1,2-trichloroethane, 1,1,1,2-tetrachloroethane, 1,1,2,2-tetrachloroethane, pentachloroethane, 1,1-dichloroethylene, cis-1,2-dichloroethylene, trans-1,2-dichloroethylene, trichloroethylene, tetrachloroethylene, 1,2-dichloropropane, and the like. Among these, methylene chloride, trans-1,2-dichloroethylene, and trichloroethylene are more preferable.

As the HFCs used as the organic compound (A), chained or cyclic HFCs having 4 to 8 carbons are preferable, and the HFCs having fluorine atoms in one molecule equal to or more than hydrogen atoms are more preferable. Specific examples of the HFCs include 1,1,1,3,3-pentafluorobutane, 1,1,1,2,2,3,4,5,5,5-decafluoropentane, 1,1,2,2,3,3,4-heptafluorocyclopentane, 1,1,1,2,2,3,3,4,4-nonafluorohexane, 1,1,1,2,2,3,3,4,4,5,5,6,6-tridecafluorohexane, 1,1,1,2,2,3,3,4,4,5,5,6,6-tridecafluorooctane, and the like. Among these, 1,1,1,2,2,3,4,5,5,5-decafluoropentane, 1,1,1,2,2,3,3,4,4-nonafluorohexane, 1,1,1,2,2,3,3,4,4,5,5,6,6-tridecafluorohexane are preferable.

As the HFEs used as the organic compound (A), $C_4F_9OCH_3$, $C_3F_7OCH_3$, 1,1,2,2-tetrafluoroethoxy-1-(2,2,2-trifluoro)ethane (HFE-347pc-f), and the like are preferable.

In one embodiment, it is further preferred that the organic compound (A) is a compound that does not have a flash point. Examples of compounds that do not have a flash point include HFCs such as 1,1,1,2,2,3,4,5,5,5-decafluoropentane, 1,1,1,2,2,3,3,4,4-nonafluorohexane, 1,1,1,2,2,3,3,4,4,5,5,6,6-tridecafluorohexane, and HFEs such as 1,1,2,2-tetrafluoroethoxy-1-(2,2,2-trifluoro)ethane. When a compound having a flash point is used as the organic compound (A), it is preferable to use the compound so as not to have a flash point as the solvent composition of the present invention.

[Additive Agent (B)]

The solvent composition of the present invention may contain an additive agent (B) to the extent that the effects of the present invention are not impaired. In one embodiment, the additive agent (B) is included in 0.0001 mass % or more, in another embodiment in 0.001 mass % or more, in another embodiment in 0.01 mass % or more, in another embodiment in 0.1 mass % or more, in another embodiment in 1 mass % or more, and in another embodiment in 3 mass % or more, for the total amount of the solvent composition of the present invention. In one embodiment, the additive agent (B) is included in 10 mass % or less, in another embodiment, in 5 mass % or less, in another embodiment, in 3 mass % or less, in another embodiment, in 1 mass % or less, in another embodiment, in 0.1 mass % or less, in another embodiment, in 0.01 mass % or less, and in another embodiment, in 0.001 mass % or less for the total amount of the solvent composition of the present invention.

In the solvent composition of the present invention, the content of the additive agent (B) may be 0.0001 mass % or more and 10 mass % or less, 0.0001 mass % or more and 5 mass % or less, 0.0001 mass % or more and 3 mass % or less, 0.0001 mass % or more and 1 mass % or less, 0.0001 mass % or more and 0.1 mass % or less, 0.0001 mass % or more and 0.01 mass % or less, 0.0001 mass % or more and 0.001 mass % or less, 0.001 mass % or more and 10 mass % or less, 0.001 mass % or more and 5 mass % or less, 0.001 mass % or more and 3 mass % or less, 0.001 mass % or more and 1 mass % or less, 0.001 mass % or more and 0.1 mass % or less, 0.001 mass % or more and 0.01 mass % or less, 0.01 mass % or more and 10 mass % or less, 0.01 mass % or more and 5 mass % or less, 0.01 mass % or more and 3 mass % or less, 0.01 mass % more and 1 mass % or less, 0.01 mass % or more and 0.1 mass % or less, 0.1 mass % or more and 10 mass % or less, 0.1 mass % or more and 5 mass % or less, 0.1 mass % or more and 3 mass % or less, 0.1 mass % or more and 1 mass % or less, 1 mass % or more and 10 mass % or less, 1 mass % or more and 5 mass % or less, 1 mass % or more and 3 mass % or less, 3 mass % or more and 10 mass % or less, 3 mass % or more and 5 mass % or less, 5 mass % or more and 10 mass % or less for the total amount of the solvent composition of the present invention.

Examples of the additive agent (B) include a stabilizer, a surfactant, a flame retardant, a metal-passivating agent, and a corrosion-inhibitor and the like. It is preferable that these additive agents (B) are appropriately selected in accordance with various applications of the solvent composition of the present invention.

(Stabilizer)

In one embodiment, the solvent composition of the present invention may contain a stabilizer to inhibit degradation of the composition even under harsh conditions, such as heat conditions. Examples of such stabilizers include nitro compounds, epoxy compounds, phenols, imidazoles, amines, phosphorus compounds, sulfur compounds, nitrogen-containing alcohol compounds, diene-based compounds, aromatic unsaturated hydrocarbons, isoprenes, propadienes, terpenes, and the like. The stabilizer may be one kind or two or more kinds.

Specific examples of nitro compounds used as the stabilizer include aliphatic nitro compounds such as nitromethane, nitroethane, 1-nitropropane, 2-nitropropane, etc., and aromatic nitro compounds such as nitrobenzene, o-, m- or p-dinitrobenzene, trinitrobenzene, o-, m- or p-nitrotoluene, o-, m- or p-ethylnitrobenzene, 2,3-, 2,4-, 2,5-, 2,6-, 3,4- or 3,5-dimethylnitrobenzene, o-, m- or p-nitroacetophenone, o-, m- or p-nitrophenol, o-, m- or p-nitroanisole.

Specific examples of the epoxy compound used as the stabilizer include monoepoxy compounds such as ethylene oxide, 1,2-butylene oxide, propylene oxide, styrene oxide, cyclohexene oxide, glycidol, epichlorohydrin, glycidyl methacrylate, phenylglycidyl ether, allylglycidyl ether, methylglycidyl ether, butylglycidyl ether, 2-ethylhexylglycidyl ether, and the like, and polyepoxy compounds such as diepoxybutane, vinylcyclohexenedioxide, neopentylglycol diglycidyl ether, ethylene glycol diglycidyl ether, glycerun polyglycidyl ether, trimethylolpropane triglycidyl ether, and the like.

The phenolic used as the stabilizer may have a substituent such as an alkyl group, an alkenyl group, an alkoxy group, a carboxyl group, a carbonyl group, halogen and the like in addition to a hydroxyl group. Specific examples of the phenols include univalent phenols such as 2,6-di-t-butyl-p-cresol, o-cresol, m-cresol, p-cresol, thymol, p-t-butyl phenol, o-methoxyphenol, m-methoxyphenol, p-methoxyphenol, eugenol, isoeugenol, butylated hydroxyanisole, phenol, xylenol, etc. and divalent phenols such as t-butyl catechol, hydroquinone, methylhydroquinone, t-butylhydroquinone, 2,5-di-t-amylhydroquinone, 2,5-di-t-butylhydroquinone, 2,2'-methylene-bis(4-methyl-6-t-butylphenol) and 2,2'-methylene-bis (4-ethyl-6-t-butylphenol) and the like.

Imidazoles used as the stabilizer, imidazoles having a hydrocarbon group having 1 to 18 carbon atoms as a substituent at the N position are preferable. The hydrocarbon group may be chain, cyclic, and may be a saturated hydrocarbon group, or may be an unsaturated hydrocarbon group. Examples of imidazoles include 1-methylimidazole, 1-n-butylimidazole, 1-phenylimidazole, 1-benzylimidazole, 1-(β-oxyethyl)imidazole, 1-methyl-2-propylimidazole, 1-methyl-2-isobutylimidazole, 1-n-butyl-2-methylimidazole, 1,2-dimethylimidazole, 1,4-dimethylimidazole, 1,5-dimethylimidazole, 1,2,5-trimethylimidazole, 1,4,5-trimethylimidazole, 1-ethyl-2-methylimidasole, 2-mercaptobenzimidazole, and the like.

Specific examples of amines used as the stabilizer include pentylamine, hexylamine, diisopropylamine, diisobutylamine, di-n-propylamine, diallylamine, triethylamine, N-methylaniline, pyridine, morpholine, N-methylmorpholine, triallylamine, allylamine, α-methylbenzylamine, methylamine, dimethylamine, trimethylamine, ethylamine, diethylamine, propylamine, isopropylamine, dipropylamine, butylamine, isobutylamine, dibutylamine, tributylamine, dibenzylamine, tribenzylamine, 2-ethylhexylamine, aniline, N,N-dimethylaniline, N,N-diethylaniline, ethylenediamine, propylenediamine, diethylenetriamine, tetraethylenepentamine, benzylamine, diphenylamine, diethylhydroxylamine, diphenylamine, 4-aminodiphenylamine, N-phenyl-1-naphthylamine, phenothiazine, and the like.

Specific examples of phosphorus compounds used as the stabilizer include triphenyl phosphite, isodecyl diphenyl phosphite, phenyldiisodecyl phosphite, tris(nonylphenyl) phosphite, and tris(2,4-di-t-butylphenyl)phosphite and the like.

Specific examples of sulfur compounds used as the stabilizer include 3,3'-thiodipropionate didodecyl, 3,3'-thiodipropionate ditetradecyl, 3-(dodecylthio)propionic acid, 3,3'-thiodipropionate dioctadecyl, and the like.

Specific examples of nitrogen-containing alcohol compounds used as the stabilizer include N-stearyl-N,N',N'-tris (polyoxyethylene)-1,3-diaminopropane, ethylenediamine-N,N'-diethanol, ethylenediamine-N,N,N',N'-tetra-2-propanol, triethylenetetramine-N-2-propanol, xylenediamine-N-2-propanol, alkylolamide, oleic acid triethanolamine ester, laurylamine-N,N-diethanol, stearylamine-N,N-diethanol, oleylamine-N,N-diethanol, bis(2-hydroxyethyl) soyamine, oleic acid dialcohol amide, stearyl aminopropyl amino ethanol, 1,3-propylenediamine-N—$C_{12-18}$-alkyl-N'-ethanol and the like.

Specific examples of the aromatic unsaturated hydrocarbons used as the stabilizer include α-methylstyrene, p-isopropenyltoluene and the like.

(Surfactants)

In one embodiment, the solvent composition of the present invention can further improve detergency, interfacial action, etc. by including a surfactant. Such surfactants include cationic surfactants, nonionic surfactants, anionic surfactants, amphoteric surfactants and the like. The surfactant may be one kind or two or more kinds.

Examples of preferred cationic surfactants include quaternary ammonium salts such as dodecyldimethylammonium chloride, trimethylammonium chloride, and the like. Examples of preferable nonionic surfactants include surfactants such as polyoxyalkylene nonylphenyl ether, polyoxyalkylene alkyl ether, fatty acid alkanolamide, glycerol fatty acid ester, sorbitan fatty acid ester, sucrose fatty acid ester, propylene glycol fatty acid ester, esters of phosphoric acid and fatty acid and the like. Examples of preferred anionic surfactants include alkyl sulfate ester salts such as polyoxyethylene alkyl sulfate salts, and the like, carboxylates such as fatty acid salts (soaps), and the like, sulfonates such as α-olefin sulfonates, lauryl sulfate, and the like. Examples of preferred amphoteric surfactants include betaine compounds such as alkyl betaines and the like.

(Flame Retardants)

In one embodiment, the solvent composition of the present invention may include a flame retardant to improve non-flammability. Examples of such flame retardants include phosphates, halogenated aromatic compounds, fluorinated iodocarbons, fluorinated bromocarbons, and the like.

[Other Components]

The solvent composition of the present invention may contain other components as long as the effects of the present invention are not impaired. The other components are not particularly limited as long as they are other than the above-mentioned components, that is, 1232xd, 1231xd, the organic compound (A), and the additive agent (B). For example, impurities derived from the above-mentioned components may be contained. Examples of such impurities include, but are not limited to, the raw materials used in the manufacturing process of the above-mentioned components.

<Cleaning Agent>

The solvent composition of the present invention has adequate fluidity and solubility and is therefore suitable for flushing and dissolving to remove foreign matter from articles.

Materials for the article include metals, resins, rubbers, fibers, glasses, ceramics, and composites thereof. Examples of composites include a laminate of metals and resins, and the like. Specific examples of the articles include, but are not limited to, precision mechanical components, electronic materials (such as print substrate, liquid crystal displays, magnetic recording components, semiconductor materials, etc.), resinous processed components, optical lenses, textiles, medical instruments, and the like.

Examples of the foreign matter include, but are not limited to, grease, processing oil, silicone oil, fat, flux, wax, ink, mineral oil, a release agent including silicone oil, and the like, dust, liquid droplets, water droplets, and the like.

In the cleaning of various vehicles, vehicles, and transportation such as automobiles, motorcycles, bicycles, construction machinery, agricultural machinery, aircraft, railway vehicles, and marine vessels (in particular, the brake cleaning thereof), the process of wetting and rinsing off the dirt is required. The composition of the present invention is suitable for such cleaning because it has an appropriate boiling point and can wet and rinse off the dirt.

The cleaning process of the article is not particularly limited, but the article is contacted with the solvent composition of the present invention or an aerosol composition described below. For example, the article to be cleaned may be immersed in the solvent composition of the present invention to rinse off the dirt, wiped off the dirt with a waste cloth, spray-cleaned, and the like, and combinations thereof may be used. It is a particularly preferable embodiment to place the solvent composition in an ultrasonic cleaning machine, immerse the article to be cleaned in the liquid, and carry out ultrasonic cleaning treatment. Also, spray cleaning, e.g., the method, in which the solvent composition of the present invention is mixed with an injection gas, the mixture is aerosolized and the aerosolized mixture is splayed to the various articles, is also one of the preferred embodiments.

<Aerosol Composition>

The inventive solvent composition may be mixed with the injection gas to form an aerosol composition.

As the injection gas, liquefied gas or compressed gas can be used. Examples include, but are not limited to, gases, such as LPG (liquefied petroleum gas), DME (dimethyl ether), carbon dioxide, chlorofluorocarbon gas, nitrogen gas, compressed air, and the like, a combination of two or more of the above gases, such as a mixture of LPG and DME, a mixture of LPG and carbon dioxide, and the like.

The aerosol composition of the present invention can be produced by mixing the solvent composition of the present invention and the above-mentioned injection gas and can be provided with filling a pressure-resistant can.

<For Dry-Cleaning>

The solvent composition of the present invention is suitable as a cleaning agent for textiles, i.e. as a dry-cleaning agent. Textile products include clothing such as shirts, sweaters, jackets, skirts, trousers, jumpers, gloves, mufflers, stools, and the like. The solvent composition of the present invention is particularly suitable for dry-cleaning of textiles comprising acrylic fibers.

The process of dry-cleaning a textile using the solvent composition of the present invention includes removing soils adhering to the textile surface by contacting the composition with the textile surface. In this case, it is preferable to use the aforementioned surfactant as the additive agent in the composition of the present invention.

<Diluted Solution>

The solvent composition of the present invention or the aerosol composition is suitable as a diluent for diluting various chemicals. In one embodiment of the diluent, the solvent composition of the present invention can be mixed with a lubricant to form a lubricant solution.

<Producing Method of Dilute Solution>

Various chemicals that can be diluted by the solvent composition or the aerosol composition of the present invention are not particularly limited, and include, for example, lubricants and rust-preventive agents.

As an embodiment of the method for producing the dilute solution, a method for producing a lubricant solution will be described below. The lubricant solution can be produced by diluting a lubricant with the solvent composition of the present invention. By applying the lubricant solution to the surface of an article and then volatilizing the solvent composition of the present invention from the article, a coated article can be produced in which a coating comprising the lubricant is formed on the surface of the article. The lubricant solution of the present invention can be applied without affecting the article containing resinous materials.

Methods of applying the lubricant solution include, for example, brush application, spraying application, application by immersing the article in the lubricant solution, and application by contacting the inner wall of tubes or needles with the lubricant solution by wicking the lubricant solution.

The lubricant is used to reduce friction on the contact surface and to prevent heat generation and wear damage when two members move in contact with each other. The lubricant may be in the form of liquids (oils), semi-solids (greases), or solids. The lubricant is preferably a mineral oil-based lubricant, a synthetic oil-based lubricant, a fluorine-based lubricant, or a silicone-based lubricant from the viewpoint of excellent solubility in the compositions of the present invention. The fluorine-based lubricant is meant a lubricant having fluorine atoms in its molecules. The silicone-based lubricant is meant a lubricant comprising silicone. The lubricant contained in the lubricant solution may be one kind or two or more kinds. Each of fluorine-based lubricant and silicone-based lubricant may be used alone or in combination.

Examples of the fluorine-based lubricant include fluorine oil, fluorine grease, fluorine-based solids lubricant such as polytetrafluoroethylene powder, and the like. As the fluorine oil, a low polymer of perfluoropolyether or chlorotrifluoroethylene is preferable. For example, the product names "Krytox® GPL102" (manufactured by DuPont de Nemours, Inc.), "Dyfloil #1", "Dyfloil #3", "Dyfloil #10", "Dyfloil #20", "Dyfloil #50", "Dyfloil #100", and "Demnam S-65" (manufactured by DAIKIN INDUSTRIES, LTD), and the like are included. As the fluorine grease, fluorine oil such as perfluoropolyether or low polymer of chlorotrifluoroethylene is preferably used as a base oil, and polytetrafluoroethylene powder or other thickener is preferably mixed. For example, the product names "Krytox® Grease 240AC" (manufactured by DuPont de Nemours, Inc.), "DAIFLOIL GREASE DG-203", "Demnam L65", "Demnam L100", "Demnam L200" (manufactured by DAIKIN INDUSTRIES, LTD), "Smitech F936" (manufactured by Sumitomo Lubricant Co., Ltd.), "MOLYKOTE® HP-300", "MOLYKOTE® HP-500", "MOLYKOTE® HP-870", "MOLYKOTE® 6169", and the like are included.

Examples of the silicone-based lubricant include silicone oil and silicone grease. As the silicone oil, dimethyl silicone, methyl hydrogen silicone, methylphenyl silicone, cyclic dimethyl silicone, and modified silicone oil in which an organic group is introduced to a side chain or a terminal thereof is preferable. Examples include the product names "Shin-Etsu Silicone KF-96", "Shin-Etsu Silicone KF-965", "Shin-Etsu Silicone KF-968", "Shin-Etsu Silicone KF-868", "Shin-Etsu Silicone KF-99", "Shin-Etsu Silicone KF-50", "Shin-Etsu Silicone KF-54", "Shin-Etsu Silicone HIVACF-4", "Shin-Etsu Silicone HIVACF-5", "Shin-Etsu Silicone KF-56A", "Shin-Etsu Silicone KF-995" (manufactured by Shin-Etsu Chemical Co., Ltd.), "SH200", and "MDX4-4159" (manufactured by Toray Dow Corning Co., Ltd.) and the like. As the silicone grease, products in which various silicone oils listed above are used as base oils, thickeners such as metallic soap, and various additive agent are blended are preferable. For example, products names "Shin-Etsu Silicone G-30 Series", "Shin-Etsu Silicone G-40 Series", "Shin-Etsu Silicone FG-720 Series", "Shin-Etsu Silicone G-411", "Shin-Etsu Silicone G-501", "Shin-Etsu Silicone G-6500", "Shin-Etsu Silicone G-330", "Shin-Etsu Silicone G-340", "Shin-Etsu Silicone G-350", "Shin-Etsu Silicone G-630" (manufactured by Shin-Etsu Chemical Co., Ltd.), "MOLYKOTE® SH33L", "MOLYKOTE® 41", "MOLYKOTE® 44", "MOLYKOTE® 822M", "MOLYKOTE® 111", "MOLYKOTE® High-Vacuum Grease", "MOLYKOTE® heat transferable compound", (manufactured by Toray Dow Corning Co., Ltd.) and the like.

The content of the lubricant in the lubricant solution of the present invention is preferably 0.01 mass % or more and 50 mass % or less, more preferably 0.05 mass % or more and 30 mass % or less, and still more preferably 0.1 mass % or more and 20 mass % or less, for the total amount of the lubricant solution. If the content of the lubricant is within the above range, it is easy to adjust the thickness of the coating film when the lubricant solution is applied and the thickness of the dried lubricant coating film to an appropriate range.

<Draining Agent Use>

In one embodiment, the solvent composition of the present invention or the aerosol composition can be used as a draining agent.

<Foaming Agent Use>

The solvent composition of the present invention or the aerosol composition can be used as a foaming agent for the production of rigid polyurethane foams or polyisocyanurate foams. That is, rigid polyurethane or polyisocyanurate foams can be produced by reacting a premix of foaming agent comprising the solvent composition or the aerosol composition of the present invention, one or more polyols, catalysts, foam stabilizers, and the like with isocyanates.

The isocyanates include those of aromatic, cyclic aliphatic, chain aliphatic, and the like, and generally bifunctional ones are used. Such isocyanates include, for example, polyisocyanates such as tolylene diisocyanate, diphenylmethane diisocyanate, polymethylene polyphenyl polyisocyanate, tolylene diisocyanate, naphthalene diisocyanate, hexamethylene diisocyanate, isophorone diisocyanate, xylylene diisocyanate, hydrogenated xylylene diisocyanate, dicyclohexylmethane isocyanate and the like, as well as pre-polymeric, nulate, and urea modifications thereof. They may be used alone or in a mixture.

The polyols included in the premix include polyether-based polyols, polyester-based polyols, polyhydric alcohols, hydroxyl group-containing diethylene-based polymers, and the like, but polyether-based polyols are generally used. Also, polyester polyols and polyether polyols may be the main components, and other polyols may be used.

Examples of the polyester polyol include phthalic anhydride, waste polyester, and compounds derived from castor oil as well as a condensation polyester polyol, a lactone polyester polyol, and a polycarbonate polyol and the like.

From the viewpoints of compatibility with foaming agent, foaming property, foam physical properties, and the like, it is preferable that the hydroxyl value (OH value) of the polyester polyol is 100 mg KOH/g or more and 400 mg KOH/g or less, and the viscosity is 200 mPa·s/25° C. or more and 4000 mPa·s/25° C. or less.

As the polyether polyol, polypropylene glycol, polytetramethylene glycol, and modified forms thereof as well as compounds obtained by adding a cyclic ether such as propylene oxide, ethylene oxide, epichlorohydrin, butylene oxide and the like to a initiator of a compound containing active hydrogen such as sugars, polyhydric alcohols, alkanolamines, and the like are preferably used.

As the polyether polyol, one having a hydroxyl value of 400 mg KOH/g or more and 1000 mg KOH/g or less is usually used.

The catalyst included in the premix includes an organometallic catalyst and an organoamine catalyst. As the organometallic catalyst, an organotin compound is preferably used, and stanas octoate, stanas laurate, dibutyltin dilaurate, dibutyltin dimalate, dibutyltin diacetate, dioctyltin diacetate, and the like can be cited. The organoamine catalyst include tertiary amines such as triethylenediamine, N-ethylmorpholine, bis(2-dimethylaminoethyl) ether, N,N',N'-triethylethanolamine, and the like.

As the foam stabilizer included in the premix, an organosilicon compound-based surfactant is usually used, and SH-193, SH-195, SH-200 or SRX-253 and the like manufactured by Toray Silicone Co., Ltd., F-230, F-305, F-341, F-348 and the like manufactured by Shin-Etsu Silicone Co., Ltd., L-544, L-5310, L-5320, L-5420, L-5720 manufactured by Nippon Unicar Co., Ltd., and TFA-4200, TFA-4202 and the like manufactured by Toshiba Silicone Co., Ltd. can be cited.

Flame retardants included in the premix include tris(2-chloroethyl) phosphate, tris(2-chloropropyl) phosphate, tris(butoxyethyl) phosphate, trismethyl phosphate, trisethyl phosphate, triphenyl phosphate, tris(isopropylphenyl) phosphate, and the like, which are phosphate esters used for rigid polyurethane foams or polyisocyanurate foams.

In one embodiment, the premix may include UV inhibitors, scorch inhibitors, premix storage stabilizers, and the like. As a result, various physical properties of the rigid polyurethane foam or polyisocyanurate foam can be improved.

<Heat Transfer Medium>

In one embodiment, the solvent composition of the present invention is suitable as a heat transfer medium for refrigeration cycle systems, high temperature heat pump systems, and organic Rankine cycle systems. In some embodiments, the solvent composition of the present invention is suitable as a cleaning agent for cleaning these cycle systems.

In this specification, "refrigeration cycle system" refers to a steam compression type refrigeration cycle system comprising element equipments of at least an evaporator, a compressor, a condenser, an expansion valve, and is mainly intended for cooling. The expansion valve is a device for throttle expansion of the heat transfer medium and may be a capillary tube. In addition to the element equipments, the refrigeration cycle system may include an internal heat exchanger, a dryer, a liquid separator, an oil recovery device, and an uncondensed-gas separator. The refrigeration cycle system may be used as a refrigerator, an air conditioning system, or a cooler.

In this specification, "high-temperature heat pump cycle system" refers to a steam compression type heat pump cycle system comprising element equipments of at least an evaporator, a compressor, a condenser, an expansion valve, and is mainly intended for heating. The expansion valve is a device for throttle expansion of the heat transfer medium and may be a capillary tube. In addition to the element equipments, the high-temperature heat pump cycle system may include an internal heat exchanger, a dryer, a liquid separator, an oil recovery device, and an uncondensed-gas separator. The high-temperature heat pump cycle system may be used as a hot water supply system, a steam generation system, a heating device. The high-temperature heat pump cycle system also may utilize solar thermal energy, industrial waste heat, etc. as a heat source.

In this specification, "organic Rankine cycle system" refers to a Rankine cycle system comprising element equipments of at least an evaporator, an expander, a condenser, and a booster pump, and is intended primarily to convert thermal energy into electrical energy. In addition to the element equipments, the organic Rankine cycle system may include an inner heat exchanger, a dryer, a liquid separator, an oil recovery device, and an uncondensed-gas separator. The organic Rankine cycle system may be used as a power generator for recovering medium and low temperature heat. The organic Rankine cycle system also may utilize solar thermal energy, industrial waste heat, etc. as heat source.

<Fire Extinguishing Composition>

Fire extinguishing composition of the present invention includes at least 1232xd and nonflammable gas other than 1232xd. 1232xd may be 1232xd (Z), 1232xd (E), or a mixture of 1232xd (Z) and 1232xd (E).

The nonflammable gas in the fire extinguishing composition may include at least one selected from, for example, carbon dioxide, nitrogen, helium, argon, krypton, xenon, radon, trifluoromethane, trifluoromethane iodide, 1,1-dichloro-2,2,2-trifluoroethane, 1-chloro-1,2,2,2-trifluoroethane, pentafluoroethane, 1,1,1,2,2,3,3-hexafluoropropane, 1,1,1,2,3,3,3-hexafluoropropane, 1,1,1,2,3,3,3-heptafluoropropane, 1,1,1,2,2,3,3-heptafluoropropane, (E) 1,3,3,3-tetrafluoropropene, (E) 1-chloro-3,3,3-trifluoropropene, (Z) 1-chloro-3,3,3-trifluoropropene, 2-bromo-3,3,3-trifluoropropene, 1-bromo-3,3,3-trifluoropropene, (Z) 1,1,1,4,4,4-hexafluoro-2-butene, (E) 1,1,1,4,4,4-hexafluoro-2-butene, dodecafluoro-2-methylpentane-3-one, tetradecafluoro-2,4-dimethylpentane-3-one, and tetradecafluoro-2-methylhexane-3-one.

The nonflammable gas is preferably nonflammable gas having a boiling point lower than 1232xd.

The ratio of 1232xd to the sum of 1232xd and the nonflammable gas in the fire extinguishing composition may be, for example, 10 mol % or more and 99 mol % or less.

In one embodiment of the fire extinguishing composition of the present invention, the nonflammable gas includes carbon dioxide, and the ratio of 1232xd to the sum of 1232xd and the nonflammable gas may be 20 mol % or more and 99 mol % or less.

In one embodiment of the fire extinguishing composition of the present invention, the nonflammable gas includes nitrogen, and the ratio of 1232xd to the sum of 1232xd and the nonflammable gas may be 20 mol % or more and 99 mol % or less.

The present invention is described by the following examples, but the present invention is not limited to the following examples.

In the following description, FID % refers to the area % as analyzed by the gas chromatograph of the FID type used as the detector.

<Fluorination of 1230xd>

1. Fluorination of 1230xd in Liquid Phase

Example 1-A1

30 g (0.16 mol) of 97FID %1,2,3,3-tetrachloro-1-propene (1230xd) and 40.0 g (2.00 mol, molar ratio of 1230xd/hydrogen fluoride=about 1/12) of hydrogen fluoride were introduced into a 200-mL stainless-steel autoclave equipped with a condenser circulating 20° C. coolant and a pressure gauge and then the autoclave was heated to 120° C. When the pressure exceeded about 4 MPaG, the reaction-generated gas was extracted from the needle valve at the outlet of the condenser so as to maintain the pressure 4.0 MPaG or more and 4.5 MPaG or less. The extracted gas was passed through a fluorine resin gas washing bottle containing ice water cooled in an ice water bath to absorb acid, and the reaction product organic matter was collected by a glass trap in a dry ice acetone bath. After 3 hours from the start of the temperature rise, it was confirmed that no pressure rise was observed, and then the reactor was purged, and the extracted gas was collected in the fluorine resin gas washing bottle containing ice water cooled in the ice water bath and a glass trap in the dry ice acetone bath. After the reactor was cooled, the reaction solution in the autoclave and the collection by the glass trap in the dry ice acetone bath were all mixed in the fluorine resin gas washing bottle containing ice water, and the combined mixed solution was passed through a fluorine resin separation funnel to separate the organic matter from an aqueous phase and to collect. The amount of recovered the organic matter was 22.1 g, and the 1232xd geometric isomer ratio in the organic matter was cis:trans=93:7.

Example 1-A2

The reaction was carried out in the same manner as in the example 1-A1 except that the reaction temperature was 140° C. The amount of organic matter recovered was 21.8 g.

Example 1-A3

The reaction was carried out as in the example 1-A1 except that the reaction temperature was 160° C. and the hydrogen fluoride 80.0 g (4.00 mol, molar ratio of 1230xd/ hydrogen fluoride=about 1/24) was introduced. The amount of organic matter recovered was 19.6 g.

Example 1-A4

Reaction was carried out as in the example 1-A2 except that tin chloride (SnCl$_4$)3g) was added. The amount of organic matter recovered was 21.8 g.

Example 1-A5

The reaction was carried out in the same manner as in the example 1-A1 except that 454 g (2.53 mol) of 97FID %1,2,3,3-tetrachloro-1-propene (1230xd) and 1000.0 g (55.0 mol, molar ratio of 1230xd/hydrogen fluoride=about 1/22) of hydrogen fluoride were introduced into a 2 L stainless-steel autoclave equipped with a condenser circulating a coolant at 20° C. and a pressure gauge, and then the autoclave was heated to 160° C. The amount of organic matter recovered was 350 g.

The results of gas chromatographic analyses for the Examples 1-A1 to 1-A5 are shown in Table 1.

2. Fluorination of 1230xd in Vapor Phase

Preparation Example 1

Preparation of Fluorinated Activated Alumina 300 g of activated alumina (KHS-46 made by Sumitomo Chemical Co., Ltd.: particle size 4-6 mm, specific surface area 155 m$^2$/g) was measured, and the powder adhering to the surface was washed with water. After washing, 1150 g of 10 mass % hydrofluoric acid was slowly added to the alumina and stirred, and then the alumina was left to stand for about 4 hours. After washing with water, filtration was carried out, drying was carried out at room temperature overnight, and then drying was carried out in an electric furnace at 200° C. for 2 hours. 150 ml of the dried activated alumina was placed in a stainless-steel (SUS316) reactor tube having an inner diameter of 1 inches and a length of 40 cm, the temperature was raised to 200° C. in an electric oven while flowing nitrogen at a flow rate of 150 cc/min, and hydrogen fluoride was further flowed at a flow rate of 0.01 g per minute together with nitrogen. Although the temperature rises as this hydrogen fluoride treatment is carried out, the flow rates of nitrogen and hydrogen fluoride were adjusted so that the internal temperature did not exceed 400° C. When the exotherm had subsided, the flow rate of nitrogen was lowered to 30 cc/min, the set temperature of the electric furnace was raised by 50° C. every 30 minutes, finally raised to 400° C., and the state was maintained for 2 hours. In this manner, activated alumina treated with fluorination (hereinafter referred to as Catalyst 1) was prepared.

Preparation Example 2

Preparation of Chrome-Supported Fluorinated Alumina Catalyst 20 mass % chromium chloride aqueous solution was added to the triangular flask, and 100 mL of fluorination treated active alumina prepared in Preparation Example 1 was immersed in the solution, and then held for 3 hours. The alumina was filtered and dried under reduced pressure at 70° C. using a rotary evaporator. 100 ml of this chrome-supported alumina was charged into the cylindrical stainless-

TABLE 1

| Example | Temperature [° C.] | Hydrogen fluoride [equivalent] | Catalyst | Recovery amount [g] | Conversion yield [%] | FID % | | | |
|---|---|---|---|---|---|---|---|---|---|
| | | | | | | 1232xd | 1231xd | 1230xd | others |
| material | | | | | | — | — | 97.0 | 3.0 |
| 1-A1 | 120 | 12 | none | 22.1 | 21.7 | 23.3 | 10.1 | 84.8 | 1.8 |
| 1-A2 | 140 | 12 | none | 21.8 | 55.8 | 80.8 | 13.0 | 24.1 | 2.1 |
| 1-A3 | 160 | 24 | none | 19.6 | 75.6 | 91.7 | 3.3 | 2.8 | 1.7 |
| 1-A4 | 140 | 12 | SnCl$_4$ | 21.8 | 41 7 | 45.5 | 9.6 | 42.0 | 2.9 |
| 1-A5 | 160 | 22 | none | 350 | 92.1 | 92.1 | 4.1 | 2.6 | 1.2 |

In Table 1, "conversion yield" indicates a simple purity conversion yield of 1232xd calculated according to the following formula.

Simple purity conversion yield of 1232xd=100×(recovered organic matter×1232xdFID %/1232xd molecular weight)/ (1230xd charged amount×1230xd purity/1230xd molecular weight)

In Table 1, "—" indicates that it was not detected.

steel (SUS316) reactor tube having an inner diameter of 1-inch and a length of 40 cm equipped with an electric oven, and the temperature was raised to 200° C. while flowing nitrogen gas, and when no water outflow was observed, nitrogen gas was supplied at a flow rate of 150 cc/min and hydrogen fluoride was simultaneously supplied at a flow rate of 0.1 g/min, and the flow rates of nitrogen and hydrogen fluoride were adjusted so that the internal temperature did not exceed 400° C. When the hot spot due to the fluorination of the charged chromium-supported alumina reached the outlet end of the reactor tube, the flow rate of the nitrogen was lowered to 30 cc/min, and the set temperature of the electric furnace was raised by 50° C. every 30 minutes, and finally raised to 400° C. and held for 2 hours. In this manner, chrome-supported alumina treated with fluorination (hereinafter referred to as Catalyst 2) was prepared.

Preparation Example 3

Preparation of Chrome-Supported Fluorinated Activated Carbon 20 mass % chromium chloride aqueous solution was added to the triangular flask, and the activated carbon 100 ml was immersed in the solution, and then held for 3 hours. The activated carbon was filtered and dried under reduced pressure at 70° C. using a rotary evaporator. 100 ml of the chrome-supported activated carbon thus obtained was charged into the cylindrical stainless-steel (SUS316) reactor tube having an inner diameter of 1 inch and a length of 40 cm and equipped with an electric oven, and the temperature was raised to 200° C. while flowing nitrogen gas, and at the point when no water outflow was observed, nitrogen gas was supplied at a flow rate of 150 cc/min and hydrogen fluoride was simultaneously supplied at a flow rate of 0.1 g/min, and the flow rates of nitrogen and hydrogen fluoride were adjusted so that the internal temperature did not exceed 400° C. When the hot spot of the charged chrome-supported activated carbon by fluorination reached the outlet end of the reactor tube, the flow rate of nitrogen was lowered to 30 cc/min, and the set temperature of the electric furnace was raised by 50° C. every 30 minutes, and finally raised to 400° C. and held for 2 hours. Thus, chrome-supported fluorinated activated carbon treated with fluorination (hereinafter referred to as Catalyst 3) was prepared.

Example 1-B1

50 ml of the catalyst prepared in Preparation Example 2 was charged into a 1 inch×40 cm long stainless-steel (SUS316) reaction tube equipped with an electric oven, and the temperature of the reaction tube was raised to 250° C. while flowing nitrogen gas at a flow rate of about 30 cc/min. Nitrogen-feed was stopped and a raw material, that is, vaporized 1,2,3,3-tetrachloro-1-propene (1230xd) was introduced at a flow rate of 0.20 g/min and hydrogen fluoride at a flow rate of 0.20 g/min. The pressure was atmospheric pressure and the contact time with the catalyst was 12 seconds. When the flow rate was stabilized, 100 ml ice water trap cooled with ice water was installed at the outlet of the reaction tube, and the organic matter was recovered for about 30 minutes and the byproduct acid content was absorbed, and the weight recovery rate was calculated. The organic components subjected to acid removal were analyzed by gas chromatography. The composition of the recovered components and the conversion rate of the raw material were calculated, and the results are shown in Table 2. The calculation methods of the weight recovery rate and the raw material conversion rate are as follows.

Weight recovery rate:100×(increased amount of ice water traps [g])/(raw material [g]+hydrogen fluoride [g])

Feed conversion rate:100×(1−raw material composition FID % in recovered organic matter/raw composition FID %)

Example 1-B2

The same procedure as in Example 1-B1 was carried out except that the temperature in the reactor tube was set to 200° C.

Example 1-B3

The same procedure as in Example 1-B1 was carried out except that the temperature in the reactor tube was set to 300° C.

Example 1-B4

The same procedure as in Example 1-B1 was carried out except that the temperature in the reactor tube was set to 350° C.

The results of Examples 1-B1 to 1-B4 are shown in Table 2.

TABLE 2

| Example | Catalyst | Hydrogen fluoride [equivalent] | Temperature [° C.] | Recovery amount [wt %] | FID % | | | |
|---|---|---|---|---|---|---|---|---|
| | | | | | 1232xd | 1231xd | 1230xd | others |
| material | | | | | — | — | 98.6 | 1.4 |
| 1 B1 | Catalyst 2 | 10 | 250 | 97.6 | 90.0 | 5.1 | 2.5 | 2.4 |
| 1-B2 | Catalyst 2 | 10 | 200 | 94.3 | 84.4 | 7.3 | 6.8 | 1.5 |
| 1-B3 | Catalyst 2 | 10 | 300 | 93.9 | 87.8 | 5.6 | 3.8 | 3.3 |
| 1-B4 | Catalyst 2 | 10 | 350 | 96.2 | 85.3 | 6.9 | 3.8 | 4.0 |

Referring to Table 2, it can be seen that 1232xd can be synthesized by fluorination of 1230xd in the range of 200° C. or more and 350° C. or less.

Example 1-B5

The same procedure as in Example 1-B1 were carried out except that Catalyst 3 was charged instead of Catalyst 2.

Example 1-B6

The same procedure as in Example 1-B1 was carried out except that Catalyst 1 was charged instead of Catalyst 2.

Example 1-B7

The same procedure as in Example 1-B1 was carried out except that activated carbon (Shirasagi G2X4/6-1) 50 ml was charged as a filler instead of the catalyst 2.

The results of Example 1-B1, Example 1-B5 to Example 1-B7 are shown in Table 3.

TABLE 3

| Example | Catalyst | Hydrogen fluoride [equivalent] | Temperature [° C.] | Recovery amount | FID % 1232xd | 1231xd | 1230xd | others |
|---|---|---|---|---|---|---|---|---|
| material | | | | | — | — | 98.6 | 1.4 |
| 1-B1 | Catalyst 2 | 10 | 250 | 97.6 | 90.0 | 5.1 | 2.5 | 2.4 |
| 1-B5 | Catalyst 3 | 10 | 250 | 98.5 | 85.0 | 4.3 | 2.0 | 8.7 |
| 1-B6 | Catalyst 1 | 10 | 250 | 91.3 | 79.5 | 9.5 | 8.8 | 2.3 |
| 1-B7 | none | 10 | 250 | 98.7 | 9.0 | 21.3 | 54.1 | 15.6 |

<Synthesis of 240 da>

Example 2-1

A 2 L three-neck flask equipped with a thermometer, an inflow pipe for inflow of liquids, and a dimroth cooling tube was charged with 35 g (10 mol %) of powdery aluminium chloride and 1275 g (10.7 mol) of chloroform, and the flask was sealed with nitrogen. Thereafter, the flask was heated to an internal temperature of about 60° C. by an oil bath, 256 g (2.64 mol) of 1,2-dichloroethylene was introduced from the inflow pipe over 2 hours, and then stirred at 60° C. for 30 minutes to terminate the reaction. The reaction solution was cooled to room temperature, washed with 500 ml of 5 mass % hydrogen chloride water, and an organic phase was dried with a molecular sieve, and then the excess chloroform was separated by an evaporator. As a result, 505 g of 240 da crude product having a purity of 98FID % (a purity conversion yield of 86.5% based on 1,2-dichloroethylene) was recovered.

Example 2-2

The same procedure as in Example 2-1 was carried out except that 7.3 g (20 mol %) of aluminium chloride, 31 g (0.26 mol) of chloroform and 100 g (1.0 mol) of 1,2-dichloroethylene were used. Thus, 50 g of 240 da crude product having a purity of 92FID % (a purity conversion yield of 80.1% based on chloroform) was recovered. The other components of the 240 da crude product were heptachloropentane, except for 240 da.

Examples 2-3

The same procedure as in Example 2-1 was carried out except that 7.3 g (20 mol %) of aluminium chloride, 31 g (0.26 mol) of chloroform and 25 g (0.26 mol) of 1,2-dichloroethylene were used. As a result, 44 g of 240 da crude product having a purity of 96FID % (a purity conversion yield of 75.2% based on 1,2-dichloroethylene) was recovered. The other components of the 240 da crude product were heptachloropentane, except for 240 da.

<Synthesis of 1230xd>

Example 3

A 2 L three-neck flask equipped with a thermometer, an inflow pipe for inflow of liquids, and a dimroth cooling tube through which water was flowed was charged with 500 g (2.26 mol) of the 240 da crude product synthesized in Examples 2-1 and 3.0 g of tetrabutylammonium bromide, and the flask was cooled to about 10° C. in an ice water bath. 550 g (3.4 mol, 1.5 eq) of 25 mass % sodium hydroxide aqueous solution was added dropwise over 2 hours through a dropping funnel, followed by stirring at room temperature of about 20° C. for 18 hours. 500 ml of 10 mass % hydrogen chloride water was added to the reaction solution, followed by washing with water, washing with saturated hydrogen carbonate water, and drying with a molecular sieve. As a result, 410 g of 1230xd crude product having a purity of 97FID % was obtained.

<Detergency Test>

Example 4

Test pieces of SUS-316L (2.8 mm×10 mm×30 mm) were immersed in the oil shown in Table 4 to attach the oil. They were immersed in 10 ml of the solvent shown in Table 4 for 30 seconds, and then air drying was performed at room temperature (23° C.) for 2 minutes. The test pieces after drying were visually observed, and the detergency of each of them was evaluated according to the following criteria.

⊚: Very good. The oil is completely removed.
○: Good. Although some oil scale is observed, it has been largely removed.
X: Poor. There is considerable oil remaining.

The results are shown in Table 4.

TABLE 4

| Example | Solvent | Type of oil | Detergency evaluation |
|---|---|---|---|
| 4-1 | 1232xd(Z):1232xd(E) = 93:7 (molar ratio) | Press working oil A | ⊚ |
| 4-2 | 1232xd(Z):1232xd(E) = 93:7 (molar ratio) | Press working oil B | ⊚ |
| 4-3 | 1232xd(Z):1232xd(E) = 93:7 (molar ratio) | Working oil A | ⊚ |
| 4-4 | 1232xd(Z):1232xd(E) = 93:7 (molar ratio) | Working oil B | ⊚ |
| 4-5 | 1232xd(Z):1232xd(E) = 93:7 (molar ratio) | Rust preventive oil | ⊚ |
| 4-6 | 1232xd(Z):1232xd(E) = 93:7 (molar ratio) | Mineral oil | ⊚ |
| 4-7 | 1232xd(Z):1232xd(E) = 93:7 (molar ratio) | Silicone oil | ⊚ |
| 4-8 | 1232xd(Z):1232xd(E) = 93:7 (molar ratio) | Press working oil A | ⊚ |
| 4-3 | 1232xd(Z) | Press working oil A | ⊚ |

In Table 4, the types of oils are as follows.
Press working oil A: PG-3246 manufactured by Nihon Kohsakuyu Co., Ltd.
Press working oil B: PG-3740 manufactured by Nihon Kohsakuyu Co., Ltd.
Working oil Tool A: CF-879 manufactured by Nihon Kohsakuyu Co., Ltd.
Working oil Tool B: C-4115 manufactured by Nihon Kohsakuyu Co., Ltd.
Rust preventive oil: P-5960 manufactured by Nihon Kohsakuyu Co., Ltd.

Mineral oil: Compressor oil manufactured by Sumitomo Lubricant Co., Ltd.
Silicone Oil: KF-96-100CS manufactured by Shin-Etsu Chemical Co., Ltd.

<Solubility Test>

Example 5

10 g of the solvent shown in Table 5 and 1 g of the oil shown in Table 5 were added to a 50 ml glass sample bottle and shaken and mixed. This was allowed to stand in a laboratory controlled at room temperature (23° C.). After 30 minutes, the state of the solution was visually observed, and the solubility was evaluated according to the following criteria.

A: Very good. The oil is completely dissolved and homogeneous.
B: Some good. Some of the oil is dissolved, but two-phase separation is observed.
C: Poor. There is no oil dissolution and two-phase separation is observed.

The results are shown in Table 5.

TABLE 5

| Example | | Type of oil | Solubility evaluation |
|---|---|---|---|
| 5-1 | 1232xd(Z):1232xd(E) = 93:7 (molar ratio) | Press working oil A | A |
| 5-2 | 1232xd(Z):1232xd(E) = 93:7 (molar ratio) | Press working oil B | A |
| 5-3 | 1232xd(Z):1232xd(E) = 93:7 (molar ratio) | Working oil A | A |
| 5-4 | 1232xd(Z):1232xd(E) = 93:7 (molar ratio) | Working oil B | A |
| 5-5 | 1232xd(Z):1232xd(E) = 93:7 (molar ratio) | Rust preventive oil | A |
| 5-8 | 1232xd(Z):1232xd(E) = 93:7 (molar ratio) | Mineral oil | A |
| 5-7 | 1232xd(Z):1232xd(E) = 93:7 (molar ratio) | Silicone oil | A |

In Table 5, the types of oils are as follows.
Press working oil A: PG-3246 manufactured by Nihon Kohsakuyu Co., Ltd.
Press working oil B: PG-3740 manufactured by Nihon Kohsakuyu Co., Ltd.
Working oil A: CF-879 manufactured by Nihon Kohsakuyu Co., Ltd.
Working oil B: C-4115 manufactured by Nihon Kohsakuyu Co., Ltd.
Rust preventive oil: P-5960 manufactured by Nihon Kohsakuyu Co., Ltd.
Mineral oil: Compressor oil manufactured by Sumitomo Lubricant Co., Ltd.
Silicone Oil: KF-96-100CS manufactured by Shin-Etsu Chemical Co., Ltd.

Example 6

All solvent and oil mixtures used in Example 5 were combined and recovered. Simple distillation was carried out to obtain 1232xd having a purity of 99GC % from the recovered mixture.

What is claimed is:

1. A solvent composition comprising:
   1,2-dichloro-3,3-difluoro-1-propene,
   wherein the 1,2-dichloro-3,3-difluoro-1-propene contains both of cis-1,2-dichloro-3,3-difluoro-1-propene and trans-1,2-dichloro-3,3-difluoro-1-propene,
   and wherein a molar ratio of the cis-1,2-dichloro-3,3-difluoro-1-propene to the trans-1,2-dichloro-3,3-difluoro-1-propene in the solvent is 50.00:50.00 to 99.99:0.01.

2. The solvent composition according to claim 1, wherein the molar ratio of the cis-1,2-dichloro-3,3-difluoro-1-propene to the trans-1,2-dichloro-3,3-difluoro-1-propene in the solvent is 60.00:40.00 to 99.99:0.01.

3. The solvent composition according to claim 1, wherein the molar ratio of the cis-1,2-dichloro-3,3-difluoro-1-propene to the trans-1,2-dichloro-3,3-difluoro-1-propene in the solvent is 70.00:30.00 to 99.99:0.01.

4. The solvent composition according to claim 1, wherein the molar ratio of the cis-1,2-dichloro-3,3-difluoro-1-propene to the trans-1,2-dichloro-3,3-difluoro-1-propene in the solvent is 80.00:20.00 to 99.99:0.01.

5. The solvent composition according to claim 1, wherein the molar ratio of the cis-1,2-dichloro-3,3-difluoro-1-propene to the trans-1,2-dichloro-3,3-difluoro-1-propene in the solvent is 90.00:10.00 to 99.99:0.01.

6. The solvent composition according to claim 1, wherein the molar ratio of the cis-1,2-dichloro-3,3-difluoro-1-propene to the trans-1,2-dichloro-3,3-difluoro-1-propene in the solvent is 93.00:7.00 to 95.00:5.00.

7. The solvent composition according to claim 1, further comprising:
   at least one selected from a group consisting of 1,2,3-trichloro-3-fluoro-1-propene, an organic compound and an additive agent,
   wherein the organic compound is at least one selected from a group consisting of hydrocarbons, alcohols, ketones, ethers, esters, chlorocarbons, HFCs, and HFEs, and
   the additive agent is at least one selected from a group consisting of a stabilizer, a surfactant, and a flame retardant.

8. The solvent composition according to claim 7, wherein a content of the 1,2,3-trichloro-3-fluoro-1-propene in the solvent composition is 0.001 mass % or more and 40 mass % or less when the solvent composition comprises the 1,2,3-trichloro-3-fluoro-1-propene.

9. An aerosol composition comprising:
   the solvent composition according to claim 1; and
   an injection gas.

10. A cleaning method of a material, comprising:
    a step of contacting the material with the solvent composition according to claim 1.

11. A method for producing a lubricant solution comprising:
    diluting a lubricant with the solvent composition according to claim 1.

12. A method for producing a material with a lubricant, comprising:
    coating the lubricant solution according to claim 11 to a surface of the material; and
    forming a coating film including the lubricant on the surface of the material by volatilizing the solvent composition or the aerosol composition from the material.

13. A cleaning agent comprising the solvent composition according to claim 1.

14. A draining agent comprising the solvent composition according to claim 1.

15. A foaming agent comprising the solvent composition according to claim 1.

16. A heat transfer medium comprising the solvent composition according to claim 1.

17. An organic Rankine cycle system using the heat transfer medium according to claim 16.

18. A high-temperature heat pump cycle system using the heat transfer medium according to claim 16.

19. A refrigeration cycle system using the heat transfer medium according to claim 16.

20. A fire extinguishing composition comprising:
    the solvent composition according to claim 1; and
    at least a nonflammable gas except for 1,2-dichloro-3,3-difluoro-1-propene.

* * * * *